(12) United States Patent
Wells

(10) Patent No.: US 12,202,912 B2
(45) Date of Patent: Jan. 21, 2025

(54) BIOPOLYMERS FOR TOPICAL USE

(71) Applicant: ExoPolymer, Inc., San Carlos, CA (US)

(72) Inventor: Derek Wells, Palo Alto, CA (US)

(73) Assignee: ExoPolymer, Inc., San Carlos, CA (US)

( * ) Notice: Subject to any disclaimer, the term of this patent is extended or adjusted under 35 U.S.C. 154(b) by 0 days.

(21) Appl. No.: 18/183,517

(22) Filed: Mar. 14, 2023

(65) Prior Publication Data

US 2023/0220117 A1  Jul. 13, 2023

Related U.S. Application Data

(63) Continuation of application No. PCT/US2022/019290, filed on Mar. 8, 2022.

(60) Provisional application No. 63/251,205, filed on Oct. 1, 2021, provisional application No. 63/158,268, filed on Mar. 8, 2021.

(51) Int. Cl.
| | |
|---|---|
| *A61K 8/60* | (2006.01) |
| *A61Q 19/00* | (2006.01) |
| *A61Q 19/08* | (2006.01) |
| *C08B 11/12* | (2006.01) |

(52) U.S. Cl.
CPC ............... *C08B 11/12* (2013.01); *A61K 8/60* (2013.01); *A61Q 19/007* (2013.01); *A61Q 19/08* (2013.01)

(58) Field of Classification Search
CPC ......... C08B 11/12; C08B 37/006; A61K 8/60; A61K 35/74; A61Q 19/007; A61Q 19/08; A61Q 19/00–10
See application file for complete search history.

(56) References Cited

U.S. PATENT DOCUMENTS

| | | | |
|---|---|---|---|
| 5,514,791 | A | 5/1996 | Doherty et al. |
| 5,831,042 | A | 11/1998 | Knipper et al. |
| 6,344,346 | B1 | 2/2002 | Alami et al. |
| 7,947,295 | B2 | 5/2011 | Chowhan et al. |
| 8,076,314 | B2 | 12/2011 | McClellan et al. |
| 9,433,805 | B2 | 9/2016 | Heber et al. |
| 9,770,400 | B2 | 9/2017 | Courtois et al. |
| 2010/0074851 | A1 | 3/2010 | Dubois et al. |
| 2010/0098794 | A1 | 4/2010 | Armand |
| 2012/0053339 | A1 | 3/2012 | Clark et al. |
| 2018/0147222 | A1 | 5/2018 | Maltzahn et al. |

FOREIGN PATENT DOCUMENTS

| | | | | |
|---|---|---|---|---|
| CA | 2701323 A1 | 4/2009 | | |
| WO | WO-9318174 A1 | * 9/1993 | ............. | A23L 1/054 |
| WO | 2014044808 A2 | 3/2014 | | |
| WO | 2014147255 A1 | 9/2014 | | |
| WO | 2015063240 A1 | 5/2015 | | |

OTHER PUBLICATIONS

Srivastava, P. "Excipients for Semisolid Formulations" in Excipient Development for Pharmaceutical, Biotechnology, and Drug Delivery Systems, CRC Press, pp. 217-244. (Year: 2006).*
Deng, J. et al "Synergistic effects of soil microstructure and bacterial EPS . . . " Soil Biol. Biochem., vo 83, pp. 116-124. (Year: 2015).*
Cesaro, A. et al "Supramolecular structure of microbial polysaccharides . . . " Polymer, vol. 33, No. 19, pp. 4001-4008. (Year: 1992).*
Andrew et al., "Structural features of microbial. exopolysaccharides in relation to their antioxidant activity", Carbohydrate Research, Pergamon, GB, vol. 487, pp. 1-18 (2019).
Barnett et al., "Novel Genes and Regulators That Influence Production of Cell Surface Exopolysaccharides in Sinorhizobium meliloti", Journal of Bacteriology, vol. 200, issue 3, pp. 1-22 (2018).
Gonzalez et al., "Rhizobium meliloti exopolysaccharides: synthesis and symbiotic function" Gene, Elsevier Amsterdam, NL, vol. 179, No. 1, pp. 141-146 (1996).
Her et al. "Structural. studies of a novel. exopolysaccharide produced by a mutant of Rhizobium melioti strain Rm1021", Carbohydrate Research, Pergamon, GB, vol. 198, No. 2, pp. 305-312 (1990).
International Search Report and Written Opinion issued in Application No. PCT/2022/019290; dated Aug. 12, 2022; 15 pages.
Lehman et al., "Exopolysaccharides from Sinorhizobium meliloti Can Protect against H2O2-Dependent Damage", Journal of Bacteriology, vol. 195, No. 23, pp. 5362-5369 (2013).
Ribeiro et al., "Exopolysaccharides Produced by Rhizobium: Production, Composition and Rheological Properties", Journal of Polymer and Biopolymer Physics Chemistry, vol. 4, No. 1, pp. 1-6 (2016).
Zevenhuizen, "Succinoglycan and Galactoglucan", Carbohydrate Polymers, Applied Science Publishers, Ltd Barking, GB, vol. 33, No. 2-3, pp. 139-144(1997).
Abd et al., "Skin models for the testing of transdermal drugs" Clinical Pharmacology: Advances and Applications 8; pp. 163-176 (2016).
Bahlawane et al., "Fine-Tuning of Galactoglucan Biosynthesis in Sinorhizobium meliloti by Differential WggR (ExpG)-, PhoB-, and MucR-Dependent Regulation of Two Promoters" Journal of Bacteriology 190(10), pp. 3456-3466 (2008).
Becker et al., "Specific Amino Acid Substitutions in the Proline-Rich Motif of the Rhizobium meliloti ExoP Protein Result in Enhanced Production of Low-Molecular-Weight Succinoglycan at the Expense of High-Molecular-Weight Succinoglycan" Journal of Bacteriology 180(2), pp. 395-399 (1998).
Copetti et al., "Synergistic gelation of xanthan gum with locust bean gum: a rheological investigation" Glycoconjugate Journal 14, pp. 951-961 (1997).
De Oliveira et al. "Genetic basis for hyper production of hyaluronic acid in natural and engineered microorganisms" Microbial Cell Factories 15(119), 19 pages (2016).

(Continued)

*Primary Examiner* — Leigh C Maier
(74) *Attorney, Agent, or Firm* — McNeill PLLC

(57) ABSTRACT

Provided herein are biopolymers comprising repeating polysaccharide units, preparations of biopolymers, and topical compositions comprising biopolymers, as well as methods of use.

47 Claims, 9 Drawing Sheets

(56) References Cited

OTHER PUBLICATIONS

Essendoubi et al. "Human skin penetration of hyaluronic acid of different molecular weights as probed by Raman spectroscopy" Skin Research and Technology 22: pp. 55-62 (2016).
Franz, "Percutaneous Absorption on the Relevance of In Vitro Data" The Journal of Investigative Dermatology 64(3), pp. 190-195 (1975).
Goa et al., "Hyaluronic Acid A Review of its Pharmacology and Use as a Surgical Aid in Ophthalmology, and its Therapeutic Potential in Joint Disease and Wound Healing" Drugs 47(3), pp. 536-566 (1994).
Jegasothy et al. "Efficacy of a New Topical Nano-hyaluronic Acid in Humans" Clinical Aesthetic Dermatology 7(3), pp. 27-29 (2014).
Keller et al., "Molecular Analysis of the Rhizobium meliloti mucR Gene Regulating the Biosynthesis of the Exopolysaccharides Succinoglycan and Galactoglucan" MPMI 8(2); pp. 267-277 (1995).
Kurt et al, "Effect of xanthan and locust bean gum synergistic interaction oncharacteristics of biodegradable edible film" International Journal of Biological Macromolecules 102; pp. 1035-1044 (2017).
Martinsen et al., "Gravimetric Method for in Vitro Calibration of Skin Hydration Measurements" IEEE Transactions on Biomedical Engineering 55(2), pp. 728-732 (2008).
Oduah et al., "Heparin: Past, Present, and Future" MDPI Pharmaceuticals 9(38); 12 pages (2016).
Papakonstantinou et al., "Hyaluronic acid A key molecule in skin aging" Dermato-Endocrinology 4(3); pp. 253-258 (2012).
Pelkonen et al., "Transmission of *Streptococcus equi* Subspecies *zooepidemicus* Infection from Horses to Humans" Emerging Infectious Diseases 19(7); pp. 1041-1048 (2013).
So et al., "Comparison of International Guidelines of Dermal Absorption Tests Used in Pesticides Exposure Assessment for Operators" Toxicological Research 30(4); pp. 251-260 (2014).
Son et al., "Hyaluronan-Based Nanohydrogels as Effective Carriers for Transdermal Delivery of Lipophilic Agents: Towards Transdermal Drug Administration in Neurological Disorders" Nanomaterials 7(427); 11 pages (2017).
Vaidyanathan et al., "Engineered heparins as new anticoagulant drugs" AIChE Bioengineering & Translational Medicine 2; pp. 17-30 (2017).
Witting et al., "Interactions of Hyaluronic Acid with the Skin and Implications for the Dermal Delivery of Biomacromolecules" Molecular Pharmaceutics 12, pp. 1391-1401 (2015).
Zakeri et al. "Enhanced hyluronic acid production in *Streptococcus zooepidemicus* by over expressing HasA and molecular weight control with Niscin and glucose" Biotechnology Reports 16; pp. 65-70 (2017).
Chi et al., "Structure and molecular morphology of a novel moisturizing exopolysaccharide produced by *Phyllobacterium* sp. 921F" International Journal of Biological Macromolecules 135, pp. 998-1005 (2019).
Li et al., "Characterization of high yield exopolysaccharide produced by *Phyllobacterium* sp. 921F exhibiting moisture preserving properties" International Journal of Biological Macromolecules 101, pp. 562-568 (2017).
"Material Safety Data Sheet, 2-Mercaptoethanol", Fisher Scientific, https://en.wikipedia.org/wiki/Hydrazine, 5 pages (2023).
Ivanov et al., "Hydrazine Toxicology", NCBI Bookshelf National Library of Medicine, StatPearls Publishing, https://www.ncbi.nlm.nih.gov/books/NBK592403/, 13 pages (2023).
Wikipedia "Hydrazine" https://en.wikipedia.org/wiki/Hydrazine, 15 pages (2023).
International Search Report and Written Opinion issued in International Application No. PCT/US2022/047583; dated Feb. 27, 2023, 10 pages.
Mendrygal et al., "Environmental Regulation of Exopolysaccharide Production in Sinorhizobium meliloti" Journal of Bacteriology, 182(3), p. 599-606 (2000).
Ridout et al., "Effect of o-acyl substituents on the functional behaviour of Rhizobium meliloti succinoglycan" International Journal of Biological Macromolecules 20 (1997), pp. 1-7.

\* cited by examiner

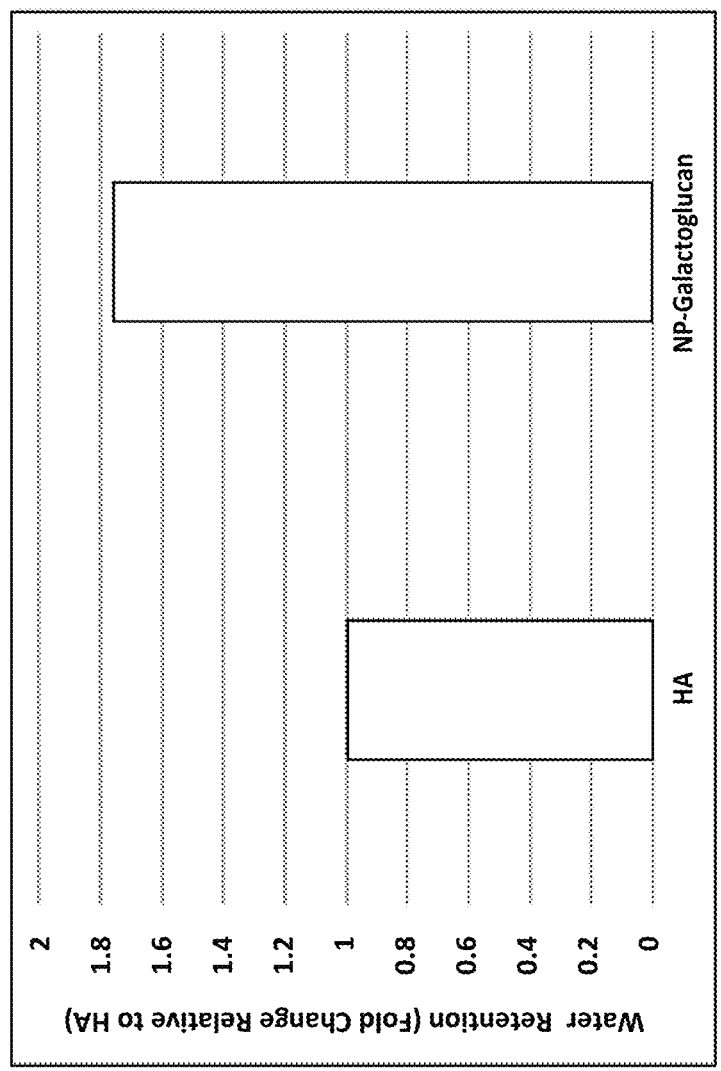
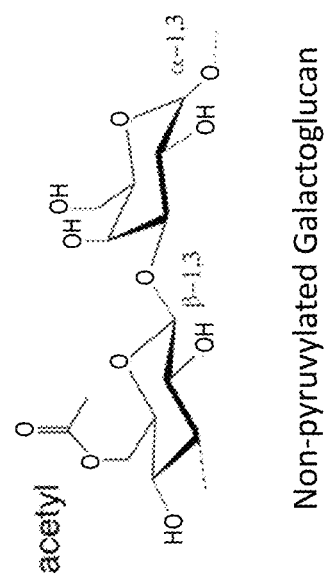
Fig. 5

RESULTS

Succinoglycan

| Test Item | Reactivity | | | | | | |
|---|---|---|---|---|---|---|---|
| | Plate 1 | Grade | Plate 2 | Grade | Plate 3 | Grade |
| Test Article | None | 0 | None | 0 | None | 0 |
| Negative Control | None | 0 | None | 0 | None | 0 |
| Positive Control | Moderate | 3 | Moderate | 3 | Moderate | 3 |

Succinoglycan/Galactoglucan

| Test Item | Reactivity | | | | | |
|---|---|---|---|---|---|---|
| | Plate 1 | Grade | Plate 2 | Grade | Plate 3 | Grade |
| Test Article | Slight | 1 | Slight | 1 | Slight | 1 |
| Negative Control | None | 0 | None | 0 | None | 0 |
| Positive Control | Moderate | 3 | Moderate | 3 | Moderate | 3 |

Galactoglucan

| Test Item | Reactivity | | | | | |
|---|---|---|---|---|---|---|
| | Plate 1 | Grade | Plate 2 | Grade | Plate 3 | Grade |
| Test Article | None | 0 | None | 0 | None | 0 |
| Negative Control | None | 0 | None | 0 | None | 0 |
| Positive Control | Moderate | 3 | Moderate | 3 | Moderate | 3 |

Glucuronoglycan

| Test Item | Reactivity | | | | | |
|---|---|---|---|---|---|---|
| | Plate 1 | Grade | Plate 2 | Grade | Plate 3 | Grade |
| Test Article | Slight | 1 | Slight | 1 | Slight | 1 |
| Negative Control | None | 0 | None | 0 | None | 0 |
| Positive Control | Moderate | 3 | Moderate | 3 | Moderate | 3 |

Kat: 0=None (No Reactivity; 1=Slight Reactivity; 2=Mild Reactivity; 3- Moderate Reactivity; 4-Severe Reactivity
Specification: The achievement of a numerical grade greater than 2 is considered a cytotoxic effect

*Fig. 6*

BIOPOLYMERS FOR TOPICAL USE

CROSS-REFERENCE TO RELATED APPLICATIONS

This application is a continuation of International Application No. PCT/US2022/019290, filed Mar. 8, 2022, which claims the benefit of priority of U.S. Provisional Application No. 63/158,268, filed Mar. 8, 2021, and U.S. Provisional Application No. 63/251,205, filed Oct. 1, 2021, each of which is incorporated by reference herein in its entirety for any purpose.

FIELD

Provided herein are biopolymers comprising repeating polysaccharide units, preparations of biopolymers, and topical compositions comprising biopolymers, as well as methods of use.

BACKGROUND

Polymers that bind and retain water are sought after in personal care and cosmetics products for their anti-aging and anti-wrinkle effects. When applied to the surface of the skin, polymers with these properties increase hydration in the epithelium. Polymers of low enough molecular weight may pass through the outer layers of skin epithelium. The ability to bind and retain water is important because increased hydration and moisture content effectively reduces the appearance of wrinkles leading to smoother and more supple skin.

The polymer most commonly used in anti-aging formulations, in particular in high-end personal care products, is hyaluronic acid (HA). HA is a high molecular weight (HMW) polymer naturally found in animal skin, connective tissue, and synovial fluid, and functions by retaining moisture and providing lubrication. It is used broadly as a dietary supplement, an injectable for joint lubrication, a surgical aid to prevent adhesion, a dermal filler, a skin surface humectant, and for the aforementioned skin-penetrating, water binding properties of LMW product in personal care and cosmetic products. HA is typically animal-derived—traditionally from rooster combs—and also as a secondary product from porcine or bovine processing facilities. It can also be produced by fermentation of *Streptococcus zooepidemicus* or related species, pathogenic bacteria that naturally incorporate HA into their cellular capsule.

Manufacturing costs for both animal- and fermentation-derived HA are high. In the case of animals, cost is driven by yields of HA per amount of tissue that are relatively low, and the several downstream processing steps required to produce the purified product. In the case of *S. zooepidemicus* HA, large scale fermentation must be performed under strictly regulated conditions, since the production organism is an infectious agent. Further, downstream processing steps may be required to reduce any potential toxins produced by the bacteria that could wind up in the final product. Finally, both products must be chemically or enzymatically processed to produce HA at molecular weights that allow for skin penetration.

Despite cost and manufacturing limitations, the HA market has continued to grow due to its robust anti-wrinkle and anti-aging performance in cosmetics. There are currently few competing technologies that provide the same or better functionality as HA. An alternative product that shows improved moisture binding, can remain on the surface or is able to penetrate the skin, and can be produced at substantially lower cost, would allow for substantial market growth and expansion. There is a need for, and lack of, moisture binding carbohydrate-based polymers to address a range of needs in the personal care and cosmetics industry.

SUMMARY

The present disclosure provides naturally produced, non-animal-derived carbohydrate biopolymers having improved moisture binding capabilities in comparison to known agents such as HA. As shown in the Examples provided herein, biopolymers of the present disclosure exhibit markedly improved moisture binding capacity relative to HA. Biopolymers of the present disclosure are particularly suited to personal care and cosmetic applications, and lack cytotoxicity in standardized testing. Furthermore, the biopolymers of the present disclosure, when used as functional ingredients in a lotion base, show improved skin hydration performance.

In some embodiments, the biopolymers of the present disclosure show transdermal penetration. In some embodiments, the biopolymers that are able to penetrate the skin are of very low molecular weight. In some embodiments, the molecular weight of penetrating biopolymers is less than 3 kDa. In some embodiments, the molecular weight of penetrating biopolymers is in the range of 3 kDa to 0.5 kDa.

Biopolymers of the present disclosure are improved over agents such as HA, at least because they are not derived from animal sources and can be made through fermentation of non-pathogenic microbes using agricultural feedstocks.

Embodiment 1. A biopolymer preparation comprising a biopolymer that is composed of repeating disaccharide units comprising glucose and galactose, wherein at least 60%, at least 65%, at least 70%, at least 75%, at least 80%, at least 85%, or at least 90% of the glucose is acetylated, and wherein at least 40%, at least 45%, at least 50%, at least 55%, at least 60%, at least 65%, at least 70%, at least 75%, at least 80%, at least 85%, at least 90%, at least 95%, or at least 99% of the galactose is pyruvylated.

Embodiment 2. The biopolymer preparation of embodiment 1, wherein the glucose and galactose are linked by β-1,3 glycosidic bonds and α-1,3 glycosidic bonds.

Embodiment 3. A biopolymer preparation comprising a biopolymer that is composed of repeating disaccharide units of the structure:

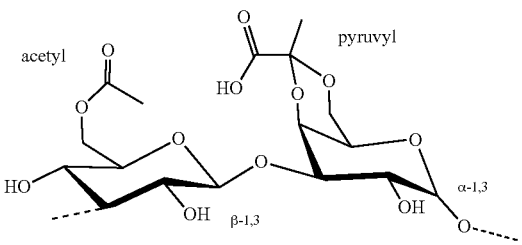

wherein the dotted lines represent the bonds between disaccharide units; wherein no more than 40%, no more than 35%, no more than 30%, no more than 25%, no more than 20%, no more than 15%, no more than 10%, or no more than 5% of the disaccharide units lack the acetyl moiety; and wherein no more than 60%, no more than 55%, no more than 50%, no more than 45%, no more than 40%, no more than 35%, no more than 30%, no more than 25%, no more than 20%, no more than 15%, no more than 10%, no more than 5%, or no more than 1% of the disaccharide units lack the pyruvyl moiety.

Embodiment 4. The biopolymer preparation of any one of embodiments 1-3, wherein the molar ratio of glucose:galactose:pyruvyl:acetyl in the biopolymer is 1:1:0.4-1:0.6-1.

Embodiment 5. The biopolymer preparation of any one of embodiments 1-4, wherein the average molecular weight of the biopolymer in the biopolymer preparation is less than 3,000 kDa, less than 1,000 kDa, less than 300 kDa, less than 100 kDa, or less than 40 kDa.

Embodiment 6. The biopolymer preparation of any one of embodiments 1-4, wherein the average molecular weight of the biopolymer in the biopolymer preparation is 0.5 kDa to 40 kDa.

Embodiment 7. The biopolymer preparation of any one of the preceding embodiments, wherein the biopolymer preparation is at least 75%, at least 80%, at least 85%, at least 90% biopolymer, or at least 95% w/w biopolymer.

Embodiment 8. The biopolymer preparation of any one of the preceding embodiments, wherein the biopolymer preparation is capable of absorbing at least the same amount, at least 1.5-fold, at least 2-fold, or at least 3-fold more water than an equal amount of hyaluronic acid.

Embodiment 9. The biopolymer preparation of any one of the preceding embodiments, wherein the biopolymer preparation is capable of absorbing an amount of water that is at least 100%, at least 200%, at least 300%, at least 400%, or at least 500% the initial dry weight of the biopolymer preparation.

Embodiment 10. The biopolymer preparation of embodiment 9 or embodiment 10, wherein water absorption is measured by placing a dry sample of the biopolymer preparation in a humidified chamber at 30° C. for five days.

Embodiment 11. The biopolymer preparation of any one of the preceding embodiments, wherein the biopolymer preparation is less than 25%, less than 20%, less than 15%, less than 10%, less than 5%, less than 3%, or less than 1% succinoglycan, or is substantially free of succinoglycan.

Embodiment 12. The biopolymer preparation of any one of the preceding embodiments, wherein the biopolymer preparation is a solid or a powder.

Embodiment 13. The biopolymer preparation of any one of the preceding embodiments, wherein the biopolymer preparation is less than 5%, less than 4%, less than 3%, less than 2%, or less than 1% water.

Embodiment 14. A biopolymer preparation comprising a biopolymer that is composed of repeating disaccharide units comprising glucose and galactose, wherein at least 60%, at least 65%, at least 70%, at least 75%, at least 80%, at least 85%, or at least 90% of the glucose is acetylated, and wherein less than 15%, less than 10%, or less than 5% of the galactose is pyruvylated.

Embodiment 15. The biopolymer preparation of embodiment 14, wherein the glucose and galactose are linked by β-1,3 glycosidic bonds and α-1,3 glycosidic bonds.

Embodiment 16. A biopolymer preparation, wherein the biopolymer is composed of repeating disaccharide units of the structure:

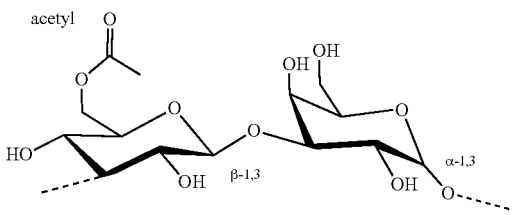

wherein the dotted lines represent the bonds between disaccharide units; wherein no more than 40%, no more than 35%, no more than 30%, no more than 25%, no more than 20%, no more than 15%, no more than 10%, or no more than 5% of the disaccharide units lack the acetyl moiety; and wherein no more than 15%, no more than 10%, or no more than 5%, of the disaccharide units are pyruvylated.

Embodiment 17. The biopolymer preparation of any one of embodiments 14-16, wherein the molar ratio of glucose:galactose:pyruvyl:acetyl in the biopolymer is 1:1:<0.5:0.6-1.

Embodiment 18. The biopolymer preparation of any one of embodiments 14-17, wherein the average molecular weight of the biopolymer in the biopolymer preparation is less than 3,000 kDa, less than 1,000 kDa, less than 300 kDa, less than 100 kDa, or less than 40 kDa.

Embodiment 19. The biopolymer preparation of any one of embodiments 14-17, wherein the average molecular weight of the biopolymer in the biopolymer preparation is 0.5 kDa to 40 kDa.

Embodiment 20. The biopolymer preparation of any one of embodiments 14-19, wherein the biopolymer preparation is at least 75%, at least 80%, at least 85%, at least 90%, or at least 95% w/w biopolymer.

Embodiment 21. The biopolymer preparation of any one of embodiments 14-20, wherein the biopolymer preparation is capable of absorbing at least the same amount, at least 1.1-fold, at least 1.2-fold, at least 1.3-fold, at least 1.4-fold, or at least 1.5-fold more water than an equal amount of hyaluronic acid.

Embodiment 22. The biopolymer preparation of any one of embodiments 14-21, wherein the biopolymer preparation is capable absorbing an amount of water that is at least 100%, at least 200%, at least 300%, or at least 400% the initial dry weight of the biopolymer preparation.

Embodiment 23. The biopolymer preparation of embodiment 21 or embodiment 22, wherein water absorption is measured by placing a dry sample of the biopolymer preparation in a humidified chamber at 30° C. for five days.

Embodiment 24. The biopolymer preparation of any one of embodiments 14-23, wherein the biopolymer preparation is less than 25%, less than 20%, less than 15%, less than 10%, less than 5%, less than 3%, or less than 1% succinoglycan.

Embodiment 25. The biopolymer preparation of any one of embodiments 14-24, wherein the biopolymer preparation is a solid or a powder.

Embodiment 26. The biopolymer preparation of any one of embodiments 14-25, wherein the biopolymer preparation is less than 5%, less than 4%, less than 3%, less than 2%, or less than 1% water.

Embodiment 27. A biopolymer preparation comprising a biopolymer that is composed of repeating polysaccharide units of the structure:

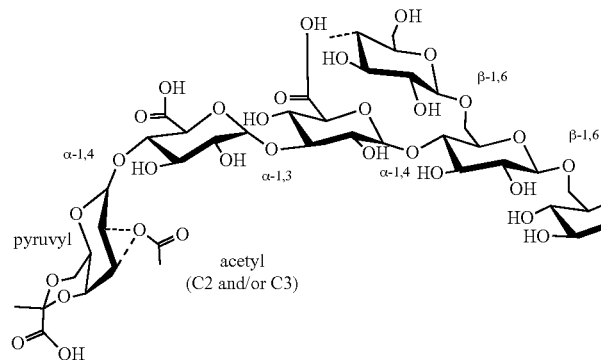
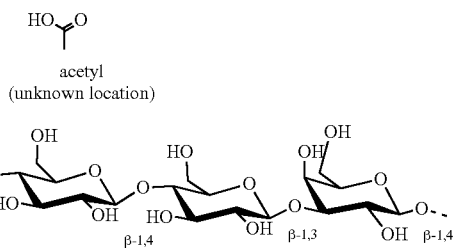

wherein the dotted lines represent the bonds between polysaccharide units; wherein no more than 30%, no more than 25%, no more than 20%, no more than 15%, no more than 10%, no more than 5%, or no more than 1% of the polysaccharide units lack an acetyl moiety; and wherein no more than 10%, no more than 5%, or no more than 1% of the polysaccharide units lack the pyruvyl moiety.

Embodiment 28. The biopolymer preparation of embodiment 27, wherein the average molecular weight of the biopolymer in the biopolymer preparation is less than 3,000 kDa, less than 1,000 kDa, less than 300 kDa, less than 100 kDa, or less than 40 kDa.

Embodiment 29. The biopolymer preparation of embodiment 27, wherein the average molecular weight of the biopolymer in the biopolymer preparation is 1.6 kDa to 40 kDa.

Embodiment 30. The biopolymer preparation of any one of embodiments 27-29, wherein the biopolymer preparation is at least 75%, at least 80%, at least 85%, at least 90% biopolymer, or at least 95% w/w biopolymer.

Embodiment 31. The biopolymer preparation of any one of embodiments 27-30, wherein the biopolymer preparation is capable of absorbing at least the same amount, at least 1.1-fold, at least 1.2-fold, at least 1.3-fold, at least 1.4-fold, or at least 1.5-fold more water than an equal amount of hyaluronic acid.

Embodiment 32. The biopolymer preparation of any one of embodiments 27-31, wherein the biopolymer preparation is capable of absorbing an amount of water that is at least 100%, at least 200%, at least 300%, or at least 400% the initial dry weight of the biopolymer preparation.

Embodiment 33. The biopolymer preparation of embodiment 31 or embodiment 32, wherein water absorption is measured by placing a dry sample of the biopolymer preparation in a humidified chamber at 30° C. for five days.

Embodiment 34. The biopolymer preparation of any one of embodiments 27-33, wherein the biopolymer preparation is a solid or a powder.

Embodiment 35. The biopolymer preparation of any one of embodiments 27-34, wherein the biopolymer preparation is less than 5%, less than 4%, less than 3%, less than 2%, or less than 1% water.

Embodiment 36. A biopolymer preparation comprising a biopolymer that is composed of repeating polysaccharide units, wherein each polysaccharide unit comprises 2-15 or 2-12 or 2-10 monosaccharides, and wherein the biopolymer has a negative charge:monosaccharide ratio in the repeating polysaccharide unit of at least 0.3, or at least 0.35, or at least 0.4, or at least 0.45.

Embodiment 37. The biopolymer preparation of embodiment 36, wherein the polysaccharide unit comprises at least one galactose linked to at least one glucose.

Embodiment 38. The biopolymer preparation of embodiment 37, wherein at least one galactose is linked to a glucose through a β-1,3 glycosidic bond.

Embodiment 39. The biopolymer preparation of any one of embodiments 36-38, wherein the average molecular weight of the biopolymer in the biopolymer preparation is less than 3,000 kDa, less than 1,000 kDa, less than 300 kDa, less than 100 kDa, or less than 40 kDa.

Embodiment 40. The biopolymer preparation of any one of embodiments 36-38, wherein the average molecular weight of the biopolymer in the biopolymer preparation is 0.5 kDa to 40 kDa.

Embodiment 41. The biopolymer preparation of any one of embodiments 36-40, wherein the biopolymer preparation is at least 75%, at least 80%, at least 85%, at least 90%, or at least 95% w/w biopolymer.

Embodiment 42. The biopolymer preparation of any one of embodiments 36-41, wherein the biopolymer preparation is capable of absorbing at least the same amount, at least 1.1-fold, at least 1.5-fold, at least 2-fold, or at least 3-fold more water than an equal amount of hyaluronic acid.

Embodiment 43. The biopolymer preparation of any one of embodiments 36-42, wherein the biopolymer preparation is capable of absorbing an amount of water that is at least 100%, at least 200%, at least 300%, or at least 400% the initial dry weight of the biopolymer preparation.

Embodiment 44. The biopolymer preparation of embodiment 42 or embodiment 43, wherein water absorption is measured by placing a dry sample of the biopolymer preparation in a humidified chamber at 30° C. for five days.

Embodiment 45. The biopolymer preparation of any one of embodiments 36-44, wherein the biopolymer preparation is a solid or a powder.

Embodiment 46. The biopolymer preparation of any one of embodiments 36-45, wherein the biopolymer preparation is less than 5%, less than 4%, less than 3%, less than 2%, or less than 1% water.

Embodiment 47. A topical composition comprising a biopolymer, wherein the biopolymer is composed of repeating disaccharide units comprising glucose and galactose, wherein at least 60%, at least 65%, at least 70%, at least 75%, at least 80%, at least 85%, or at least 90% of the glucose is acetylated, and wherein at least 40%, at least 45%, at least 50%, at least 55%, at least 60%, at least 65%, at least 70%, at least 75%, at least 80%, at least 85%, at least 90%, at least 95%, or at least 99% of the galactose is pyruvylated.

Embodiment 48. The topical composition of embodiment 47, wherein the glucose and galactose are linked by β-1,3 glycosidic bonds and α-1,3 glycosidic bonds.

Embodiment 49. A topical composition comprising a biopolymer, wherein the biopolymer is composed of repeating disaccharide units of the structure:

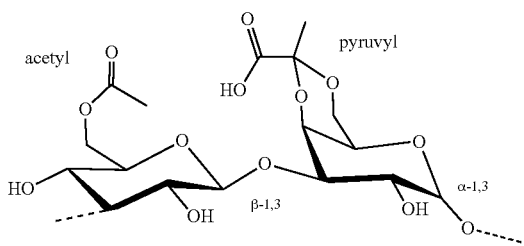

wherein the dotted lines represent the bonds between disaccharide units; wherein no more than 40%, no more than 35%, no more than 30%, no more than 25%, no more than 20%, no more than 15%, no more than 10%, or no more than 5% of the disaccharide units lack the acetyl moiety; and wherein no more than 60%, no more than 55%, no more than 50%, no more than 45%, no more than 40%, no more than 35%, no more than 30%, no more than 25%, no more than 20%, no more than 15%, no more than 10%, no more than 5%, or no more than 1% of the disaccharide units lack the pyruvyl moiety.

Embodiment 50. The topical composition of any one of embodiments 47-49, wherein the molar ratio of glucose:galactose:pyruvyl:acetyl in the biopolymer is 1:1:0.4-1:0.6-1.

Embodiment 51. The topical composition of any one of embodiments 47-50, wherein the average molecular weight of the biopolymer in the topical composition is less than 3,000 kDa, less than 1,000 kDa, less than 300 kDa, less than 100 kDa, or less than 40 kDa.

Embodiment 52. The topical composition of any one of embodiments 47-51, wherein the average molecular weight of the biopolymer in the topical composition is 0.5 kDa to 40 kDa.

Embodiment 53. The topical composition of any one of embodiments 47-53, wherein the biopolymer is capable of absorbing at least the same amount, at least 1.5-fold, at least 2-fold, or at least 3-fold more water than an equal amount of hyaluronic acid.

Embodiment 54. The topical composition of any one of embodiments 47-53, wherein the biopolymer is capable of absorbing an amount of water that is at least 100%, at least 200%, at least 300%, at least 400%, or at least 500% the initial dry weight of the biopolymer.

Embodiment 55. The topical composition of embodiment 53 or embodiment 54, wherein water absorption is measured by placing a dry sample of the biopolymer in a humidified chamber at 30° C. for five days.

Embodiment 56. The topical composition of any one of embodiments 47-55, wherein the topical composition comprises the biopolymer preparation of any one of embodiments 1-13.

Embodiment 57. The topical composition of any one of embodiments 47-56, which is substantially free of succinoglycan.

Embodiment 58. A topical composition comprising a biopolymer, wherein the biopolymer is composed of repeating disaccharide units comprising glucose and galactose, wherein at least 60%, at least 65%, at least 70%, at least 75%, at least 80%, at least 85%, or at least 90% of the glucose is acetylated, and wherein less than 15%, less than 10%, or less than 5% of the galactose is pyruvylated.

Embodiment 59. The topical composition of embodiment 58, wherein the glucose and galactose are linked by β-1,3 linkages and α-1,3 linkages.

Embodiment 60. A topical composition comprising a biopolymer, wherein the biopolymer is composed of repeating disaccharide units of the structure:

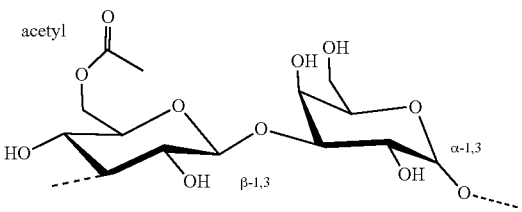

wherein the dotted lines represent the bonds between disaccharide units; wherein no more than 40%, no more than 35%, no more than 30%, no more than 25%, no more than 20%, no more than 15%, no more than 10%, or no more than 5% of the disaccharide units lack the acetyl moiety; and wherein no more than 15%, no more than 10%, or no more than 5%, of the disaccharide units are pyruvylated.

Embodiment 61. The topical composition of any one of embodiments 58-60, wherein the molar ratio of glucose:galactose:pyruvyl:acetyl in the biopolymer is 1:1:<0.5:0.6-1.

Embodiment 62. The topical composition of any one of embodiments 58-61, wherein the average molecular weight of the biopolymer in the topical composition is less than 3,000 kDa, less than 1,000 kDa, less than 300 kDa, less than 100 kDa, or less than 40 kDa.

Embodiment 63. The topical composition of any one of embodiments 58-61, wherein the average molecular weight of the biopolymer in the topical composition is 0.5 kDa to 40 kDa.

Embodiment 64. The topical composition of any one of embodiments 58-63, wherein the biopolymer preparation is capable of absorbing at least the same amount, at least 1.1-fold, at least 1.2-fold, at least 1.3-fold, at least 1.4-fold, or at least 1.5-fold more water than an equal amount of hyaluronic acid.

Embodiment 65. The topical composition of any one of embodiments 58-64, wherein the biopolymer preparation is capable absorbing an amount of water that is at least 100%, at least 200%, at least 300%, or at least 400% the initial dry weight of the biopolymer.

Embodiment 66. The topical composition of embodiment 64 or embodiment 65, wherein water absorption is measured by placing a dry sample of the biopolymer in a humidified chamber at 30° C. for five days.

Embodiment 67. The topical composition of any one of embodiments 58-66, wherein the topical composition comprises the biopolymer preparation of any one of embodiments 14-26.

Embodiment 68. The topical composition of any one of embodiments 58-67, which is substantially free of succinoglycan.

Embodiment 69. A topical composition comprising a biopolymer, wherein the biopolymer is composed of repeating polysaccharide units of the structure:

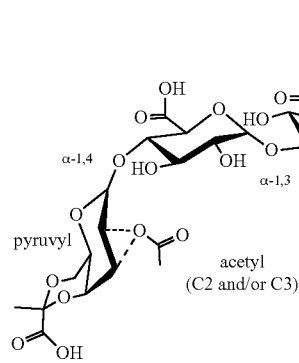
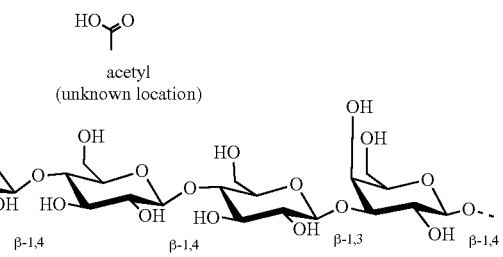

wherein the dotted lines represent the bonds between polysaccharide units; wherein no more than 30%, no more than 25%, no more than 20%, no more than 15%, no more than 10%, no more than 5%, or no more than 1% of the polysaccharide units lack an acetyl moiety; and wherein no more than 10%, no more than 5%, or no more than 1% of the polysaccharide units lack the pyruvyl moiety.

Embodiment 70. The topical composition of embodiment 69, wherein the average molecular weight of the biopolymer in the topical composition is less than 3,000 kDa, less than 1,000 kDa, less than 300 kDa, less than 100 kDa, or less than 40 kDa.

Embodiment 71. The topical composition of embodiment 69, wherein the average molecular weight of the biopolymer in the topical composition is 1.6 kDa to 40 kDa.

Embodiment 72. The topical composition of any one of embodiments 69-71, wherein the biopolymer preparation is capable of absorbing at least the same amount, at least 1.1-fold, at least 1.2-fold, at least 1.3-fold, at least 1.4-fold, or at least 1.5-fold more water than an equal amount of hyaluronic acid.

Embodiment 73. The topical composition of any one of embodiments 69-72, wherein the biopolymer preparation is capable of absorbing an amount of water that is at least 100%, at least 200%, at least 300%, or at least 400% the initial dry weight of the biopolymer.

Embodiment 74. The topical composition of embodiment 72 or embodiment 73, wherein water absorption is measured by placing a dry sample of the biopolymer in a humidified chamber at 30° C. for five days.

Embodiment 75. The topical composition of any one of embodiments 69-74, wherein the topical composition comprises the biopolymer preparation of any one of embodiments 27-35.

Embodiment 76. A topical composition comprising a biopolymer, wherein the biopolymer is composed of repeating polysaccharide units, wherein each polysaccharide unit comprises 2-15 or 2-12 or 2-10 monosaccharides, and wherein the biopolymer has a negative charge:monosaccharide ratio in the repeating polysaccharide unit of at least 0.3, or at least 0.35, or at least 0.4, or at least 0.45.

Embodiment 77. The topical composition of embodiment 76, wherein the polysaccharide unit comprises at least one galactose linked to at least one glucose.

Embodiment 78. The topical composition of embodiment 77, wherein at least one galactose is linked to a glucose through a β1,3 glycosidic bond.

Embodiment 79. The topical composition of any one of embodiments 76-78, wherein the average molecular weight of the biopolymer in the topical composition is less than 3,000 kDa, less than 1,000 kDa, less than 300 kDa, less than 100 kDa, or less than 40 kDa.

Embodiment 80. The topical composition of any one of embodiments 76-78, wherein the average molecular weight of the biopolymer in the topical composition is 0.5 kDa to 40 kDa.

Embodiment 81. The topical composition of any one of embodiments 76-80, wherein the biopolymer preparation is capable of absorbing at least the same amount, at least 1.1-fold, at least 1.5-fold, at least 2-fold, or at least 3-fold more water than an equal amount of hyaluronic acid.

Embodiment 82. The topical composition of any one of embodiments 76-81, wherein the biopolymer preparation is capable of absorbing an amount of water that is at least equal to, at least 1.5 times, at least two times, at least 2.5 times, at least three times, at least four times, or at least five times the initial dry weight of the biopolymer.

Embodiment 83. The topical composition of embodiment 81 or embodiment 82, wherein water absorption is measured by placing a dry sample of the biopolymer in a humidified chamber at 30° C. for five days.

Embodiment 84. The topical composition of any one of embodiments 76-83, wherein the topical composition comprises the biopolymer preparation of any one of embodiments 36-46.

Embodiment 85. The topical composition of any one of embodiments 47-84, wherein the topical composition comprises 0.01-10% w/w or 0.05%-5% w/w of the biopolymer.

Embodiment 86. The topical composition of any one of embodiments 47-85, wherein the topical composition comprises one or more viscosifiers, stabilizers, emulsifiers, emollients, humectancts, rheology modifiers, film formers, antioxidants, additives, actives, butters, essential oils, infused oils, clays, muds, extracts, hydrosol waters, exfoliants, supplements, waxes, thickeners, salts, minerals, acids, bases, carrier and fixed oils, surfactants, preservatives, pearlizers, conditioning agents, structuring agents, whitening agents, moisturizers, osmolytes, occlusives, cleansers, colorants, pigments, fragrances, UV-A and UV-B screens, and/or nourishing agents.

Embodiment 87. The topical composition of any one of embodiments 47-86, wherein the topical composition comprises hyaluronic acid.

Embodiment 88. The topical composition of any one of embodiments 47-86, wherein the topical composition does not comprise hyaluronic acid.

Embodiment 89. The topical composition of any one of embodiments 47-88, wherein the topical composition is a cream, lotion, ointment, balm, tincture, liniment, shampoo, soap, conditioner, sunscreen, rinse, deodorant, or cosmetic.

Embodiment 90. A method of treating or preventing a skin condition in a subject, comprising applying the topical composition of any one of embodiments 47-89.

Embodiment 91. The method of embodiment 90, wherein the skin condition is one or more of dry skin, wrinkled skin, sagging skin, aged skin, scarred skin, injured skin, blemished skin, acne, and/or sunburned skin.

Embodiment 92. The method of embodiment 90, wherein the skin condition is an inflammatory skin condition.

Embodiment 93. The method of embodiment 92, wherein the inflammatory skin condition is psoriasis, eczema, or atopic dermatitis.

Embodiment 94. The method of any one of embodiments 90-93, wherein the topical composition is applied to the face, ears, forehead, neck, arms, upper chest, and/or hands of the subject.

Embodiment 95. The method of any one of embodiments 90-94, wherein the topical composition reduces transepidermal water loss, reverses transepidermal water loss, improves epidermal water retention, reduces appearance of wrinkles, reduces skin sagging, increases skin smoothness, increases swelling of the skin, improves skin suppleness, improves skin texture, reduces skin blemishes, and/or reduces skin dryness.

BRIEF DESCRIPTION OF THE DRAWINGS

FIG. 5. Water absorption of non-pyruvylated galactoglucan compared to HA. The ability to bind water was measured as described in Example 4 and FIG. 3. Mass increase was normalized to the value for HA, and fold change was calculated.

FIG. 6. Cytotoxicity of biopolymers. Cytotoxicity testing was performed according to the ISO 10993-5 standard. Biopolymers were dissolved in PBS at a concentration of 1% (w/v), heat pasteurized, and used in cytotoxicity assays. Values for each biopolymer were compared to both positive and negative controls.

DETAILED DESCRIPTION

Figure 1:
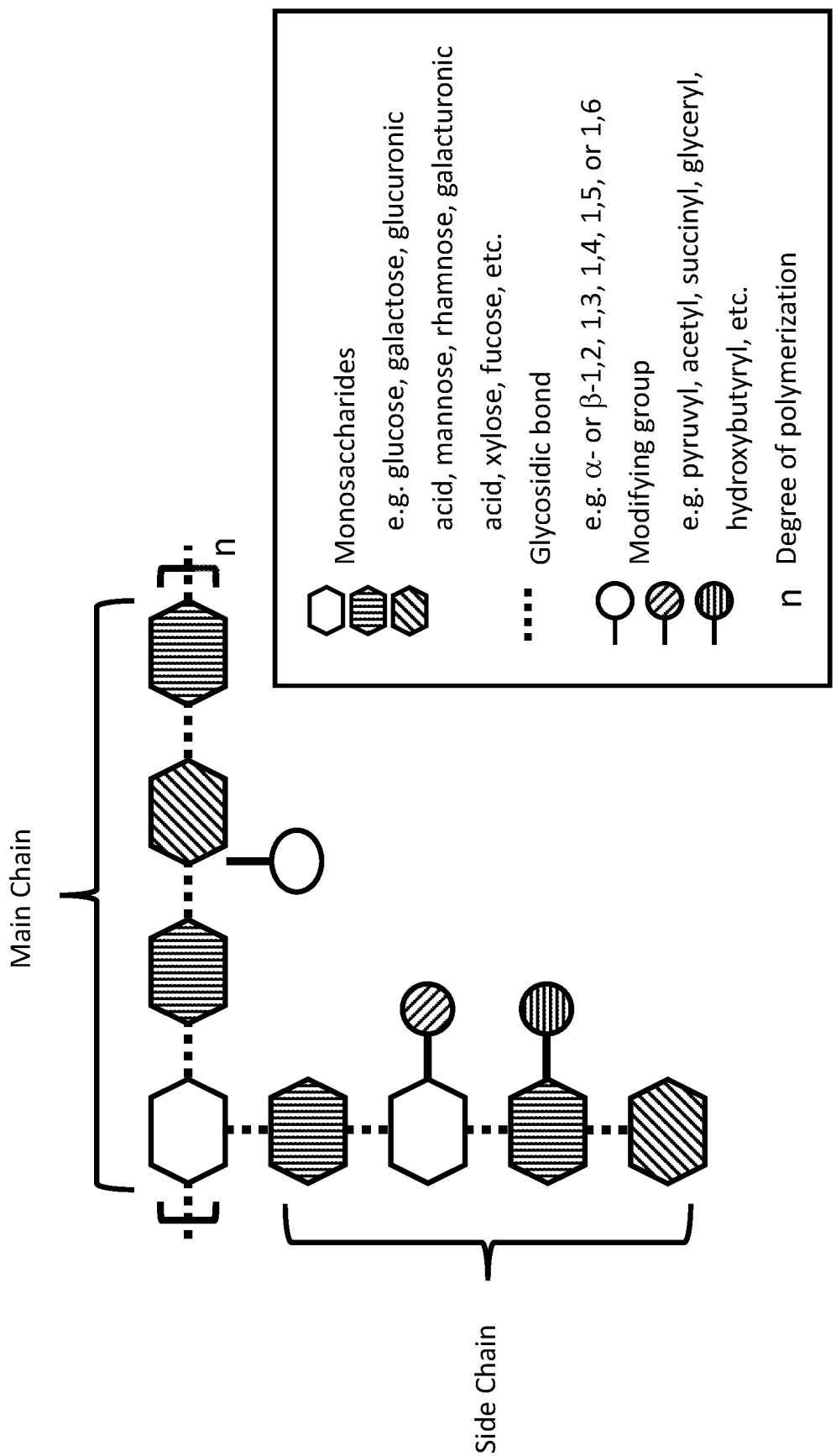
FIG. 1. Representative repeating unit of a polysaccharide biopolymer. Individual sugar residues are linked by glycosidic bonds. Polysaccharide-based biopolymers consist of a main chain of sugar residues that are connected by glycosidic linkages. The main chain may also have a side chain consisting of sugar residues, and each may have different chemical modifications. The main and side chains of a biopolymer, along with chemical modifications, make up a repeating unit. Repeating units are connected by glycosidic linkages to generate longer polymers.

Natural product biopolymers with improved moisture binding properties, that are low molecular weight (LMW) and produced by the fermentation of non-pathogenic microbes, are attractive for a number of different reasons. First, such biopolymers are more cost-effective to produce than traditional hyaluronic acid and can be added at higher concentrations in personal care and cosmetics products to achieve improved anti-wrinkle and anti-aging performance. Second, these biopolymers can be added to a substantially wider range of personal care products such as lip balms, shaving creams, sunscreen, shampoos, conditioners, and soaps, where skin penetration and hydration provides improved performance. Third, a biopolymer that is produced by microbial fermentation is an attractive alternative to animal-derived HA and mitigates social and/or moral issues associated with animal use. Biopolymers from harmless microbes, as opposed to pathogenic ones, require fewer downstream processing steps to manufacture a safe product. Last, biopolymers that are naturally produced at LMW have substantial advantages over the current processes for the manufacture of LMW HA, which require several additional downstream processing steps to achieve performance specifications.

The present invention provides compositions and the cosmetic and/or dermatological or pharmaceutical use of biopolymers based on exopolysaccharides produced by non-pathogenic species of soil bacteria. High water binding capacity and skin retention/penetration are desirable properties of personal care ingredients with anti-aging and anti-wrinkle effects. The most broadly used polymer with these properties is hyaluronic acid, which is derived either from animals or pathogenic bacteria. Provided herein are isolated biopolymers that have substantially improved water binding properties in comparison to hyaluronic acid. In some embodiments, the isolated biopolymers are derived from Rhizobiaceae bacteria. These bacteria naturally produce low molecular weight biopolymers, which have the ability to penetrate the skin. Manufacture of these biopolymers by fermentation is highly advantaged relative to the processes for hyaluronic acid production.

The present inventors have identified certain biopolymers that have water retention properties superior to those of HA, and are thus ideal for use as anti-aging products in a wide range of personal care and cosmetics formulations. The first molecule, galactoglucan, is a repeating disaccharide of galactose and glucose with pyruvyl and acetyl modifications. It is derived from the bacterium Sinorhizobium meliloti (aka Ensifer meliloti) and is naturally produced at low molecular weight (LMW) during fermentation. It is one of two biopolymers that are naturally produced by this organism, and its moisture binding properties can only be observed independently of the other biopolymer, succinoglycan. We have demonstrated that galactoglucan has greater than 3.5× the water retention capacity of HA. A variant of galactoglucan, which lacks the pyruvyl modification, shows 1.7× the water retention capacity of HA. The second molecule, glucuronoglycan, is a repeating nonasaccharide containing galactose, glucuronic acid, and glucose with pyruvyl and acetyl modifications. It is derived from the bacterium Sinorhizobium fredi (aka Ensifer fredii) and is naturally produced as a mixture of high and low molecular weights. We have demonstrated that glucuronoglycan has 1.7× the water retention capacity of HA.

In addition to the increased water retention performance, galactoglucan and glucuronoglycan are non-toxic in a standard pre-clinical model, a prerequisite for suitability of the compounds in cosmetic and dermatological uses. In some embodiments, these LMW biopolymer fractions penetrate through skin samples in an in vitro Franz cell assay. In personal care formulations, in some embodiments, the inclusion of Rhizobiaceae-derived biopolymers in representative lotion bases provides improved hydration to the skin.

This invention provides microbial polymers with beneficial performance features—moisture retention, skin surface retention, and/or penetration—for use as anti-aging and anti-wrinkle ingredients in personal care and cosmetic formulations. These microbial biopolymers show substantially improved moisture retention in comparison to the industry standard active ingredient, hyaluronic acid, which is used in many skin care products for its anti-aging properties. The Rhizobiaceae-derived biopolymers described herein are suitable for use in a wide range of water-based skin care formulations, and can provide increased efficacy in skin hydration in many consumer products. Further, the production of LMW biopolymers by fermentation, requiring little downstream processing, provides an economically advantaged method of production compared to incumbent technologies for the manufacture of animal- or microbial-derived HA of specified molecular weights.

Biopolymers and Biopolymer Preparations

The Rhizobiaceae, a family of soil-dwelling, symbiotic bacteria, have been studied for decades for their ability to provide fixed nitrogen to their leguminous plant hosts, but to date have not been fully exploited as fermentative microorganisms for the production of bioindustrial, pharmaceutical, or cosmetic products. These bacteria naturally produce water-soluble exopolysaccharides, or biopolymers, which have roles in both host plant association and biofilm formation. The variety of exopolysaccharides produced by the Rhizobiaceae suggests a breadth of novel biopolymers with new functionalities that could add substantial value to several markets.

Succinoglycan and Galactoglucan

Sinorhizobium (Ensifer) meliloti naturally produces two acidic exopolysaccharides: succinoglycan (EPS I), and galactoglucan (EPS II) (Barnett 2018). Succinoglycan is the major exopolysaccharide produced by S. meliloti. The repeating unit of succinoglycan (FIG. 2) consists of glucose and galactose in a 7:1 ratio with acetyl, pyruvyl and succinyl modifications (Reuber 1993). Succinoglycan is naturally produced by S. meliloti at both high and low molecular weights. The general mechanism of succinoglycan biosynthesis is relatively well understood and likely shared by related organisms that produce similar biopolymers.

Galactoglucan production is restricted to species that are phylogenetically close to S. meliloti. The repeating unit of galactoglucan (FIG. 2) consists of glucose and galactose in a 1:1 ratio with acetyl and pyruvyl modifications (Glazebrook 1989). Specific linkages are $\beta$-D-Glcp-(1-3)-$\alpha$-D-Galp-(1-3), with a 6-O-acetyl on most D-glucose residues, and a 4,6-O-pyruvyl on every D-galactose (Her 1990). Galactoglucan is naturally produced by S. meliloti at low molecular weights. In comparison to succinoglycan, relatively little is known about the biosynthetic pathway of galactoglucan.

Glucuronoglycan

Figure 2:
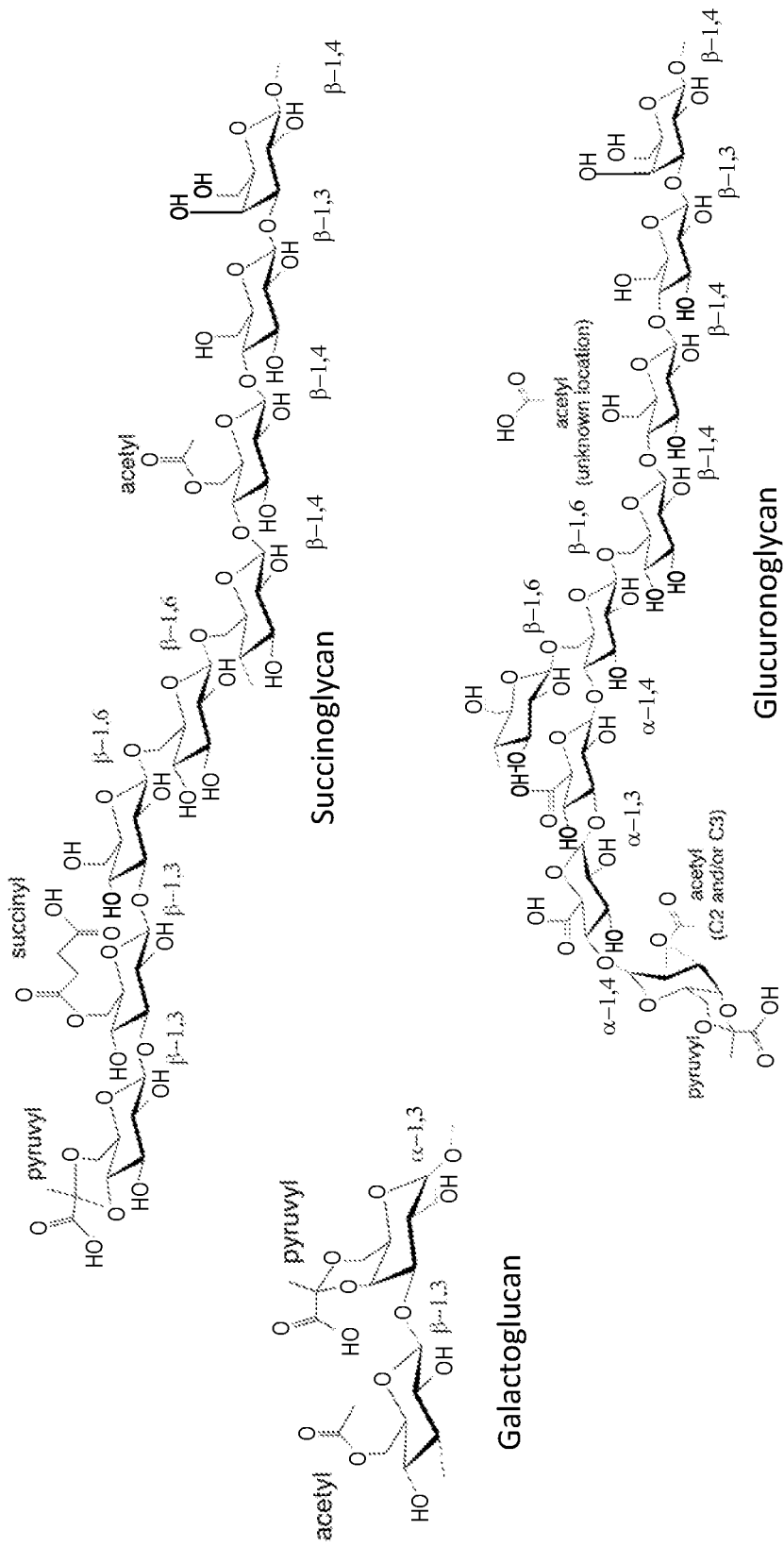
FIG. 2. Biopolymer structures. Galactoglucan is a repeating dimer of galactose and glucose, with pyruvyl and acetyl modifications. Succinoglycan is a repeating octamer of one galactose and seven glucose residues, with pyruvyl, acetyl, and succinyl modifications. Glucuronoglycan is a repeating nonamer of two galactose, two glucuronic acid, and five glucose residues with pyruvyl and acetyl modifications.

Sinorhizobium (Ensifer) fredii naturally produces an acidic exopolysaccharide that consists of glucose, galactose, and glucuronic acid in a 5:2:2 ratio with acetyl and pyruvyl modifications (Djordjevic 1986) (FIG. 2). The biopolymer depicted in FIG. 2 is produced by several S. fredii type strains including NGR234, HH103 (ATCC51809), and likely USDA257 (Gray 1991, Pueppke 1999, Rodriguez-Navarro 2014). According to structural analyses, the terminal galactose on the side chain of glucuronoglycan is 4,6-pyruvylated, and it can be acetylated on either the second, third, or both carbons of the same sugar residue. A third acetyl group has also been detected in glucuronoglycan from the HH103 strain, and therefore likely the other strains as well, but its location has not been elucidated (Staehelin 2006, Rodriguez-Navarro 2014). The exo region of these S. fredii species spans 28 kb and shares a high degree of synteny with the S. meliloti cluster responsible for succinoglycan biosynthesis. Many of the genes share homology with the S. meliloti exo genes (Zhan 1990). Glucuronoglycan has a similar structure to succinoglycan, but contains glucuronic acid and is not succinylated. The main chain of glucuronoglycan consists of six sugar residues, whereas that of succinoglycan contains four. Glucuronoglycan is produced by S. fredii strains at both high and low molecular weights (Staehelin 2006).

In some embodiments, a biopolymer is provided that is composed of repeating disaccharide units comprising glucose and galactose, wherein at least 60%, at least 65%, at least 70%, at least 75%, at least 80%, at least 85%, or at least 90% of the glucose is acetylated, and wherein at least 40%, at least 45%, at least 50%, at least 55%, at least 60%, at least 65%, at least 70%, at least 75%, at least 80%, at least 85%, at least 90%, at least 95%, or at least 99% of the galactose is pyruvylated. In some embodiments, the glucose and galactose are linked by $\beta$-1,3 glycosidic bonds and $\alpha$-1,3 glycosidic bonds. In some embodiments, a biopolymer is provided that is composed of repeating disaccharide units of the structure:

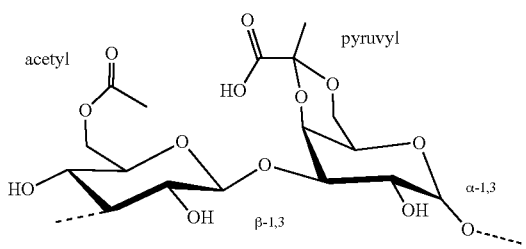

wherein the dotted lines represent the bonds between disaccharide units; wherein no more than 40%, no more than 35%, no more than 30%, no more than 25%, no more than 20%, no more than 15%, no more than 10%, or no more than 5% of the disaccharide units lack the acetyl moiety; and wherein no more than 60%, no more than 55%, no more than 50%, no more than 45%, no more than 40%, no more than 35%, no more than 30%, no more than 25%, no more than 20%, no more than 15%, no more than 10%, no more than 5%, or no more than 1% of the disaccharide units lack the pyruvyl moiety. In some embodiments, the biopolymer is comprised in a biopolymer preparation. In some such embodiments, the molar ratio of glucose:galactose:pyruvyl:acetyl in the biopolymer preparation is 1:1:0.4-1:0.6-1. In some embodiments, a preparation of the biopolymer is provided that comprises less than 25%, less than 20%, less than 15%, less than 10%, less than 5%, less than 3%, or less than 1% succinoglycan. In some embodiments, a preparation of the biopolymer is substantially free of succinoglycan.

In some embodiments, a biopolymer is provided that is composed of repeating disaccharide units comprising glucose and galactose, wherein at least 60%, at least 65%, at least 70%, at least 75%, at least 80%, at least 85%, or at least 90% of the glucose is acetylated, and wherein less than 15%, less than 10%, or less than 5% of the galactose is pyruvylated. In some embodiments, the glucose and galactose are linked by β-1,3 glycosidic bonds and α-1,3 glycosidic bonds. In some embodiments, a biopolymer is provided that is composed of repeating disaccharide units of the structure:

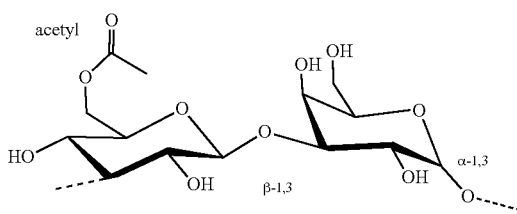

wherein the dotted lines represent the bonds between disaccharide units; wherein no more than 40%, no more than 35%, no more than 30%, no more than 25%, no more than 20%, no more than 15%, no more than 10%, or no more than 5% of the disaccharide units lack the acetyl moiety; and wherein no more than 15%, no more than 10%, or no more than 5%, of the disaccharide units are pyruvylated. In some embodiments, the biopolymer is comprised in a biopolymer preparation. In some such embodiments, the molar ratio of glucose:galactose:pyruvyl:acetyl in the biopolymer preparation is 1:1:<0.5:0.6-1. In some embodiments, a preparation of the biopolymer is provided that comprises less than 25%, less than 20%, less than 15%, less than 10%, less than 5%, less than 3%, or less than 1% succinoglycan. In some embodiments, a preparation of the biopolymer is substantially free of succinoglycan.

In some embodiments, a biopolymer is provided, wherein the biopolymer is composed of repeating polysaccharide units of the structure:

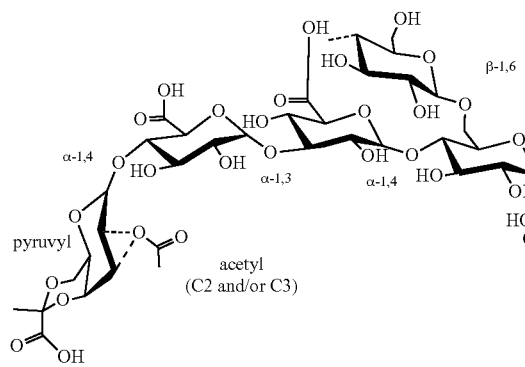

wherein the dotted lines represent the bonds between polysaccharide units; wherein no more than 30%, no more than 25%, no more than 20%, no more than 15%, no more than 10%, no more than 5%, or no more than 1% of the polysaccharide units lack an acetyl moiety; and wherein no more than 10%, no more than 5%, or no more than 1% of the disaccharide units lack the pyruvyl moiety. In some embodiments, a polysaccharide unit comprises one, two, are three acetyl groups. In some embodiments, the average number of acetyl groups per polysaccharide unit is 1-3.

In some embodiments, a biopolymer is provided, wherein the biopolymer is composed of repeating polysaccharide units, wherein each polysaccharide unit comprises 2-15 or 2-12 or 2-10 monosaccharides, and wherein the biopolymer has a negative charge:monosaccharide ratio in the repeating polysaccharide unit of at least 0.3, or at least 0.35, or at least 0.4, or at least 0.45. In some embodiments, the polysaccharide unit comprises at least one galactose linked to at least one glucose. In some such embodiments, at least one galactose is linked to a glucose through a β-1,3 glycosidic bond.

In various embodiments, a biopolymer preparation is provided, wherein the biopolymer preparation is at least 75%, at least 80%, at least 85%, at least 90%, or at least 95% w/w of a biopolymer provided herein. In some embodiments, a biopolymer preparation is a solid or a powder. In some embodiments, a biopolymer preparation is less than 5%, less than 4%, less than 3%, less than 2%, or less than 1% water.

In various embodiments, the average molecular weight of the biopolymer in the biopolymer preparation is less than 3,000 kDa, less than 1,000 kDa, less than 300 kDa, less than 100 kDa, or less than 40 kDa. In some embodiments, the average molecular weight of the biopolymer in the biopolymer preparation is 0.5 kDa to 40 kDa or 1.6 kDa to 40 kDa.

In some embodiments, the biopolymer is capable of absorbing at least the same amount, at least 1.1-fold, at least 1.2-fold, at least 1.3-fold, at least 1.4-fold, 1.5-fold, at least 2-fold, or at least 3-fold more water than an equal amount of hyaluronic acid. In some embodiments, the biopolymer is capable of absorbing an amount of water that is at least 100%, at least 200%, at least 300%, at least 400%, or at least 500% the initial dry weight of the biopolymer preparation. Water absorption may be measured, for example, by placing a dry sample of the biopolymer or a biopolymer preparation in a humidified chamber at an approximately constant temperature for a fixed length of time. In some embodiments, the temperature is about 20° C., about 25° C., about 30° C., about 35° C., or about 37° C. In some embodiments, the fixed length of time is one day, two days, three days, four days, five days, six days, or one week.

Strain Construction

Both S. meliloti and S. fredii are amenable to genetic modification, and a common method for strain engineering is to use homologous recombination, antibiotic resistance, and sucrose counter selection (Quandt 1993) to delete specific regions in the genome. Plasmids that contain modified genomic regions can be constructed and then used to replace native regions with targeted changes. By introduction of these non-replicating plasmids by conjugal transfer, strains with single integrations can be selected by antibiotic resistance and confirmed by PCR. Secondarily, integrated plasmids can be counter selected due the presence of the socB gene, which encodes a levansucrase that is lethal to Gram negative bacteria in the presence of sucrose. Antibiotic sensitive, sucrose resistant strains will then either have recombined to wild type, or have incorporated a deletion, insertion, or other modification that was present in the constructed plasmid. Modified strains can be confirmed by PCR and sequencing.

Unmodified, non-domesticated strains of S. meliloti produce both succinoglycan and galactoglucan, and are suitable for the simultaneous production of both biopolymers. In certain type strains, such as Rm1021 (ATCC51124), the ability to produce galactoglucan has been lost due to lab strain domestication (Charoenpanich 2015). In the case of domesticated strains, there are several methods by which a galactoglucan producing strain can be constructed. Examples include restoration of an intact expR gene, knock out of mucR, overexpression of WggR (Bahlawane 2008), or growth in phosphate-limited medium (Mendrygal 2000).

For the production of succinoglycan in the absence of galactoglucan, the type strain Rm1021 can be used. There are several regulatory genes which can be modified resulting in strains which overproduce succinoglycan. These genes include exoR, exoS, chvI, syrM, and nodD3 (Barnett 2015). Others include syrA, mucR (Keller 1995), and exoX (Zhan 1990). If a non-domesticated strain of S. meliloti is used, it is necessary to knock out galactoglucan biosynthetic genes to generate a strain that only produces succinoglycan. The genes required for galactoglucan biosynthesis fall within a 32 kb region of pSymB and include six predicted glycosyltransferases and four genes predicted to encode proteins required for the synthesis of dTDP-glucose and dTDP-rhamnose (Becker 1997). Any of several glycosyltransferases, such as wgaB or wgeB may be excised in order to eliminate production of galactoglucan.

To produce galactoglucan in the absence of succinoglycan, wild type strains of S. meliloti with mutations in succinoglycan biosynthetic genes can be generated using pJQ200SK. Additionally, domesticated strains with the restored ability to produce galactoglucan, via any of the methods described above, may be used. The biosynthetic cluster specific for succinoglycan is located within a 22 kb region on pSymB. Structural and regulatory roles have been assigned to several of the genes in this cluster (Reuber 1993). To eliminate succinoglycan biosynthesis, any of several genes, such as exoA, exoF, exoL, exoM, exoP, exoQ, exoT, or exoY, may be excised genetically.

Glucuronoglycan is the major product of wild type S. fredii, and no modifications of strains are necessary for the production of this biopolymer. Any of the strains mentioned above may be used for production and further analysis of material.

Methods of Making Biopolymers

For production of biopolymers, several different liquid growth media can be used. S. meliloti strains grow well on LB or TY medium, and these can be supplemented with an additional carbon source such as glucose, sucrose, or succinate to boost production of product. S. fredii can be grown on TY medium, and supplementation with additional carbon source is beneficial to production. Both S. meliloti and S. fredii can be grown on defined minimal medium, such as M9 or MOPS-mannitol, which can result in higher yields. Minimal medium allows for precise control over fermentation variables such as phosphate concentration, pH, micronutrients, sulfate concentration, and carbon source.

Alcohol precipitation may be used to purify biopolymers after fermentation. Typically, cells are removed from fermentation broth by centrifugation or filtration. High viscosity of fermentation broth may necessitate the addition of one to two volumes of water to assist in cell separation procedures. To further remove residual cells or cell debris, the cell-free supernatant may be incubated with protease. To precipitate biopolymer, isopropanol or ethanol, as well as a mono- or divalent cation such as KCl or $CaCl_2$ in a concentration range around 1 mM, can be added to the cell-free supernatant, typically at 1× to 2× the culture volume. Biopolymers precipitate upon mixing, and can be isolated by centrifugation or filtration. Further purification steps may be undertaken at this point to reduce salt concentrations or any cell debris that may have precipitated with the polymer. These steps may include additional alcohol washes, protease treatments, rehydration, centrifugation, dialysis, solvent washes, lyophilization, etc., that suit the desired end use. Purified product can be dried in an oven until mass stabilizes (all unbound water has evaporated). Dried product can be ground, milled, or otherwise processed to generate final, purified biopolymers.

Topical Compositions

Hyaluronic acid (HA) plays a critical role in skin aging, and supplemental HA can be found in many personal care lotions and creams. In certain common formulations, HMW HA is used because it sits on the surface of the skin and hydrates by absorbing water from the atmosphere. In other formulations, LMW HA is used because it may penetrate the skin and provide anti-aging or anti-wrinkle effects. Skin penetration has been shown to be directly related to polymer length (Essendoubi 2016, Witting 2015). Penetration into sublayers of the epidermis, water binding, and skin swelling contribute to a reduction in the appearance of wrinkles. Molecules with these performances are therefore highly sought after for skin care formulations that reduce the appearance of aging.

Functional ingredients are typically found at concentrations at or below 2% (w/v) in personal care products. While higher concentrations may be more effective at improving skin appearance, raw material costs likely prohibit the inclusion of ingredients at levels higher than 2%. High cost may also prohibit use in a broader range of commonly used personal care products. Despite these limitations, there are few alternative products that can compete with the performance and efficacy of HA in dermal filler and topical anti-aging personal care formulations. Dermal filler alternatives include products such as the biomineral hydroxylapatite or petroleum-derived products such as polymethylmethacrylate. Biological alternatives include agarose, which is often used in combination with HA, polyglutamic acid (PGA) which is non-carbohydrate based, or polymers derived from tamarind seed extract.

Examples of topically applied products include any aqueous solution, alcohol, or oil-in-water emulsion such as cream, lotion, serum, ointment, balm (such as lip balm), tincture, liniment, shampoo, soap, conditioner, sunscreen, rinse, cosmetic, deodorant, or any other treatment that is used directly on skin. The topical compositions provided herein may be more or less fluid and may be in the form of salves, emulsions, creams, milks, ointments, impregnated pads, syndets, solutions, sera, gels, sprays or aerosols, foams, suspensions, lotions, or sticks.

In various embodiments, topical compositions are provided, comprising at least one biopolymer provided herein. In some embodiments, a topical composition comprises one, two, or three of the biopolymers provided herein. In some embodiments, the composition comprises 0.01-30%, 1-30%, 0.01-20%, 1-20%, 0.01-10%, or 0.05%-5% w/v of a biopolymer provided herein. In some embodiments, a topical composition comprises at least one biopolymer provided herein and hyaluronic acid. In some such embodiments, hyaluronic acid is present at a concentration of 0.01-5%, 0.01-3%, 0.01-2%, 0.01-1%, 0.1-2%, or 0.1-1% w/v.

In various embodiments, a topical composition provided herein comprises one or more pharmaceutically and/or cosmetically-acceptable viscosifiers, stabilizers, emulsifiers, emollients, humectancts, rheology modifiers, film formers, antioxidants, additives, actives, butters, essential oils, infused oils, clays, muds, extracts, hydrosol waters, exfoliants, supplements, waxes, thickeners, salts, minerals, acids, bases, carrier and fixed oils, surfactants, preservatives, pearlizers, conditioning agents, structuring agents, whitening agents, moisturizers, osmolytes, occlusives, cleansers, colorants, pigments, fragrances, UV-A and UV-B screens, and/or nourishing agents. One skilled in the art can select suitable ingredients for a topical composition based on the desired application. Many lists and descriptions of suitable ingredients are available in the art, including, for example, at cir-safety.org and/or www.fda.gov/cosmetics/cosmetic-products-ingredients. Nonlimiting exemplar viscosity and/or rheology modifiers include polyacrylates, their derivatives and copolymers, polysorbates and derivatives, myristates, polyquaterniums, cellulose and derivatives, cetearyl alcohol, carbomers, xanthan gum, diutan gum, capric glycerides, modified sugars, other polysaccharide polymers, paraffins, polyethylene glycol, glycerol, propanediol, oleic acid derivatives, and hyaluronic acid. Nonlimiting exemplary humectants include hyaluronic acid, methyl glucose ethers, ethylated methyl glucose, glycerol, polyethylene glycol, glycol derivatives, collagen, urea, sorbitol, allantoin, and alpha hydroxy acids. Nonlimiting exemplary emollients include mineral oil, lanolin, rhea butter, cocoa butter, coconut oil, beeswax, sunflower oil, other plant oils, vegetable and animal fats, petrolatum, and squalene. Additional ingredients for topical compositions include, but are not limited to, silicone derivatives (lubricants), tocopherol (Vitamin E), parabens (preservatives), stearic and oleic acids, sodium lauryl sulfate (surfactants), keratin, elastin (proteins), amino acids and peptides, and bentonite clay.

Uses of Topical Compositions

Skin is the human body's first line of defense against external challenges such as heat, infection, exposure to toxic substances, and water loss. The outermost layer of the epidermis is called the stratum corneum, which is made up of stacked, non-viable cells that are not hydrated. The primary function of the stratum corneum is to maintain skin homeostasis by preventing excessive transepidermal loss of water. Below the stratum corneum is the remainder of the epidermis, which is made up of various types of metabolically active cells such as keratinocytes and melanocytes. Below the epidermis are the dermis and hypodermis, which contain blood vessels, nerve cells, and apocrine glands (Abd 2016).

Although the stratum corneum is the primary barrier against water loss, the presence of HA in the metabolically active layers of the epidermis has been shown to be the most important factor in the overall hydration level of the skin. Aging or senescent skin is marked by both the decrease in polymer length, and general loss of polymer in the epidermis (Papakonstantinou 2012). Moisture-retaining polymers that can pass through the stratum corneum barrier and penetrate into the epidermis can potentially offset the aforementioned effects of skin aging. Creams, lotions, sera, or other topical compositions could be applied to the skin, and polymers would then penetrate into deeper layers of the epidermis, increasing the overall volume of water retained in the skin. Skin would then swell causing a general reduction in the appearance of wrinkles. Water-retaining polymers could also be used in a number of other personal care products, where additional hydration would be useful, either to counteract drying effects of other active ingredients, or to create formulations that provide additional moisturization and/or value for the consumer.

In some embodiments, methods of treating or preventing a skin condition are provided, comprising applying a topical composition that comprises a biopolymer provided herein. In some embodiments, the skin condition is one or more of dry skin, wrinkled skin, sagging skin, aged skin, scarred skin, injured skin, blemished skin, acne, and/or sunburned skin. In some embodiments, the skin condition is an inflammatory skin condition, such as psoriasis, eczema, or atopic dermatitis. In some embodiments, the skin condition is wounded skin. In some embodiments, the topical composition is applied to the face, ears, forehead, neck, arms, upper chest, legs, feet, and/or hands of the subject.

In various embodiments, application of the topical composition reduces transepidermal water loss, reverses transepidermal water loss, improves epidermal water retention, reduces appearance of wrinkles, reduces skin sagging, increases skin smoothness, increases swelling of the skin, improves skin suppleness, improves skin texture, reduces skin blemishes, and/or reduces skin dryness. In some embodiments, the improvement is determined at a second time point compared to a first time point that is immediately before the first application of the topical composition. In some embodiments, the topical composition is applied three times a day, twice a day, once a day, every other day, every three days, or once per week. In some embodiments, the topical composition is applied for a period of one week, two weeks, one month, two months, three months, six months, one year, or longer. In some embodiments, the improvement is evident after use of the topical composition for two weeks, one month, two months, three months, six months, or one year or more.

EXAMPLES

Example 1. Natural Biopolymers Produced by S. meliloti and S. fredii

Naturally occurring biopolymers produced by select Rhizobiaceae strains are shown in FIG. 2. Succinoglycan, also referred to as EPSI, is produced by *Sinorhizobium meliloti*. The repeating unit consists of a linear main chain of one galactose and three glucose monosaccharides, and a side chain of four glucose molecules. Main chain sugars are linked by β-1,3 and β-1,4 glycosidic bonds. Side chain sugars are linked by β-1,3 and β-1,6 glycosidic bonds. It is acetylated on glucose three of the main chain, succinylated on glucose three of the side chain, and pyruvylated on the terminal glucose of the side chain (Reuber 1993). Galactoglucan, also referred to as EPSII, is also produced by *S. meliloti*. It is a linear, repeating dimer of galactose and glucose linked by β-1,3 and α-1,3 glycosidic bonds (Glazebrook 1989). Galactose residues are fully pyruvylated, while approximately 70% of glucose units are acetylated (Her 1990). Glucuronoglycan is produced by *Sinorhizobium fredii*. It consists of a main chain composed of one galactose and five glucose monosaccharides linked by β-1,3, β-1,4 and β-1,6 glycosidic bonds, and a side chain of two glucuronic acids and a terminal galactose linked by α-1,3, α-1,4, and β-1,4 glycosidic bonds. The terminal galactose on the side chain is both acetylated (at carbons 2 and/or 3) and 4,6-pyruvylated (Djordjevic 1986). Glucuronoglycan can be acetylated at a third, unknown location (Rodriquez-Navarro 2014).

Example 2. Strain Construction

For targeted deletion of selected ORFs, excision of insertion elements, or correction of SNPs, a non-replicating plasmid vector with positive and negative selection markers was used. Since both *S. meliloti* and *S. fredii* are amenable to genetic modification using standard molecular biology and strain engineering techniques, this methodology allows for rapid and precise changes to their genomes to create desired genotypes. First, derivatives of the pJQ200SK plasmid (Quandt 1993) carrying deletion cassettes were generated. For deletion cassettes, regions upstream and downstream (usually 500 bp) of the target ORF including start and stop codons were amplified by PCR. For introduction of wild type DNA, regions upstream and downstream of an insertion element were amplified by PCR. Next, plasmids were assembled using the CPEC method (Quan 2009), and sequence verified prior to introduction into *S. meliloti*. Plasmids were introduced into *S. meliloti* by tri-parental mating and strains containing single integrations at homologous genomic regions were selected for antibiotic resistance, and verified by PCR using primers outside of amplified regions. Strains positive for integration of plasmids were then streaked to purification, and selected for the ability to grow on sucrose. The presence of the socB gene on the integrated pJQ200 plasmid causes lethality when strains are grown on sucrose. Strains that are propagated on sucrose will therefore have mutations in socB itself, or will recombine to "loop out" the integrated plasmid and either revert to wild type or harbor the deleted or modified sequence originally present in the plasmid.

Domesticated strains of *S. meliloti*, such as strain Rm1021, have lost the ability to produce galactoglucan (Pellock 2002), and there are several genetic modifications that can be introduced to restore this function. These modifications include deletion of the mucR gene, restoration of a wild type allele, expR101, into the expR locus (Gonzalez 1996), or introduction of a wild type expR ORF and promoter (Charoenpanich 2015). These changes all result in an Rm1021-derived strain that produces galactoglucan in addition to succinoglycan. For this study, wild type expR was introduced into strain Rm1021 using the methodology described above. This resulted in strain EXO3, which produces both *S. meliloti* biopolymers simultaneously.

Strain EXO3 was used to generate derivative strains that produced either succinoglycan or galactoglucan alone, by deleting ORFs that are known to be responsible for the biosynthesis of either exopolysaccharide. For example, a strain that produces succinoglycan can be generated by deletion of any of several glycosyltransferases, including wgoB, or wgeB involved in the synthesis of galactoglucan (Becker 1997). A strain that produces galactoglucan can be generated by deletion of any of several glycosyltransferases, such as exoF, exoA or exoY (Gonzalez 1996, Glazebrook 1989), involved in the initial steps of succinoglycan biosynthesis. Using the techniques described above, the wgeB ORF was deleted to generate an EXO3 derivative only capable of producing succinoglycan. To generate a galactoglucan production strain, the exoY ORF was deleted in EXO3. These strains, EXO1 and EXO2 (Table 1), were used for the subsequent production of succinoglycan or galactoglucan, respectively.

The targeted deletion method described above can be used to generate strains that produce variant biopolymers, such as those that lack chemical modifications. The genes responsible for succinylation and acetylation of succinoglycan, exoH and exoZ, for example, may be deleted from the genome of *S. meliloti*. To generate a modified version of galactoglucan, wgaE, the gene responsible for pyruvylation was excised from *S. meliloti*.

TABLE 1

BioPolymer production strains.

| Strain | Species | Genotype | Product |
|---|---|---|---|
| EXO1 | S. meliloti Rm1021 | expR+, ΔwgeB | Succinoglycan |
| EXO2 | S. meliloti Rm1021 | expR+, ΔexoY | Galactoglucan |
| EXO3 | S. meliloti Rm1021 | expR+ | Succinoglycan + galactoglucan |
| EXO19 | S. meliloti Rm1021 | expR+, ΔexoY, ΔwgaE | Galactoglucan (lacking pyruvate) |
| EXO5 | S. fredii NGR234 | Wild type | Glucuronoglycan |

Example 3. Production and Purification of Biopolymers

For bench scale growth and biopolymer production, batch cultures in shake flasks were used. Production strains were inoculated from culture plates into TY medium and grown overnight in a shaking incubator at 30° C. The next day, the overnight cultures were diluted, typically at a ratio of 1:100 or 1:200, into production medium. Production medium consisted of a defined minimal medium such as M9 containing a carbon source, either glucose or sucrose, at a concentration between 2-4% (w/v), a nitrogen source such as ammonium sulfate, a buffer to maintain neutral pH, divalent cations such as $MgSO_4$ and $CaCl_2$, trace elements, and vitamins (U.S. Pat. No. 7,371,558B2). Strains were grown in production medium for up to three days, and then harvested for purification.

Recovery and purification of biopolymers were performed by initial cell separation followed by alcohol precipitation. For high molecular weight polymers, cultures were diluted in either two or three volumes of water and supernatant was separated from cells by centrifugation. For low molecular weight biopolymers it was not necessary to dilute culture broth prior to cell separation. Approximately 1 mM $CaCl_2$ was then added to the supernatant, and biopolymers were precipitated at room temperature by addition of two volumes of isopropyl alcohol. Precipitates were isolated by centrifugation, and then washed in either 70% or 90% ethyl alcohol. After the wash steps, precipitates were re-isolated by low-speed centrifugation and dried overnight in a 60° C. oven until weight loss stabilized, indicating an absence of residual water. Final product was then ground using a mortar and pestle or using a bench scale mill.

Example 4. Characterization of Biopolymers

Biopolymers are characterized by analytical methods. In some instances, NMR spectroscopy may be used to determine structural information on composition, sequence distribution, substitution pattern, and molecular weights. Biopolymers may be assayed by solution-NMR or solid-state NMR. For solution-state NMR of polysaccharides, due to the high viscosity of the material, the sample may be subjected to enzymatic digestion or pretreatment (Her et al. 1990). Samples may be assayed without pre-treatment using solid-state methods, such as $^{13}C$ cross-polarization magic-angle spinning (CPMAS) NMR (Schaefer 1976). More detailed structural analysis and/or quantitation may be assessed by 2D NMR, for example as described in Yao 2021. The person of skill in the art understands that each analytical method has distinct advantages and disadvantages and can select an appropriate analytical method to generate desired information regarding the structure, extent of modification, and/or purity level of biopolymers. Using these methods, the extent of modification of sugars in a polysaccharide chain may be quantified. Levels of acetylation, pyruvylation, succinylation, or other modifying chemical groups, for example, may be determined for a sample of biopolymer.

Example 5. Water Absorption

To determine the water binding capacity of biopolymers, samples were placed in a sealed, humidified chamber for five days and mass increase was measured in comparison to hyaluronic acid. Biopolymers were purified according to the procedures in Example 3. Prior to conducting the water absorption experiments, biopolymer samples were dried for 30 minutes at 60° C. to ensure that all residual water was evaporated. Small amounts (typically between 25 and 50 mg) were then weighed (value $m_0$) and placed into individual tared plastic or aluminum trays. All samples were placed on a platform in a sealed plastic chamber containing 250 ml of warm (approximately 35 C) water. The entire chamber containing all samples was then placed into an incubator at 30° C. After five days, the humidified chamber was opened, and individual samples were weighed (value m) to calculate mass increase. Water binding capacity (WBC) for each sample was calculated according to the following equation: $(m-m_0)/m_0$. This raw value represents the degree of swelling and can be expressed as percent mass increase by multiplying by 100.

A pure, 5 kDa preparation of hyaluronic acid (HAworks) was used as a control for the water binding experiments. WBC, measured as described above, of hyaluronic acid was typically between 200 and 300%. Higher molecular weights of HA (100 kDa HAworks, and >1000 kDa Acros Organics) were tested and showed similar water absorbing capacities as the low molecular weight sample. To calculate fold change of experimental samples, WBC values for mass increase of biopolymers were normalized to the WBC values for HA within an experiment.

Figure 3:
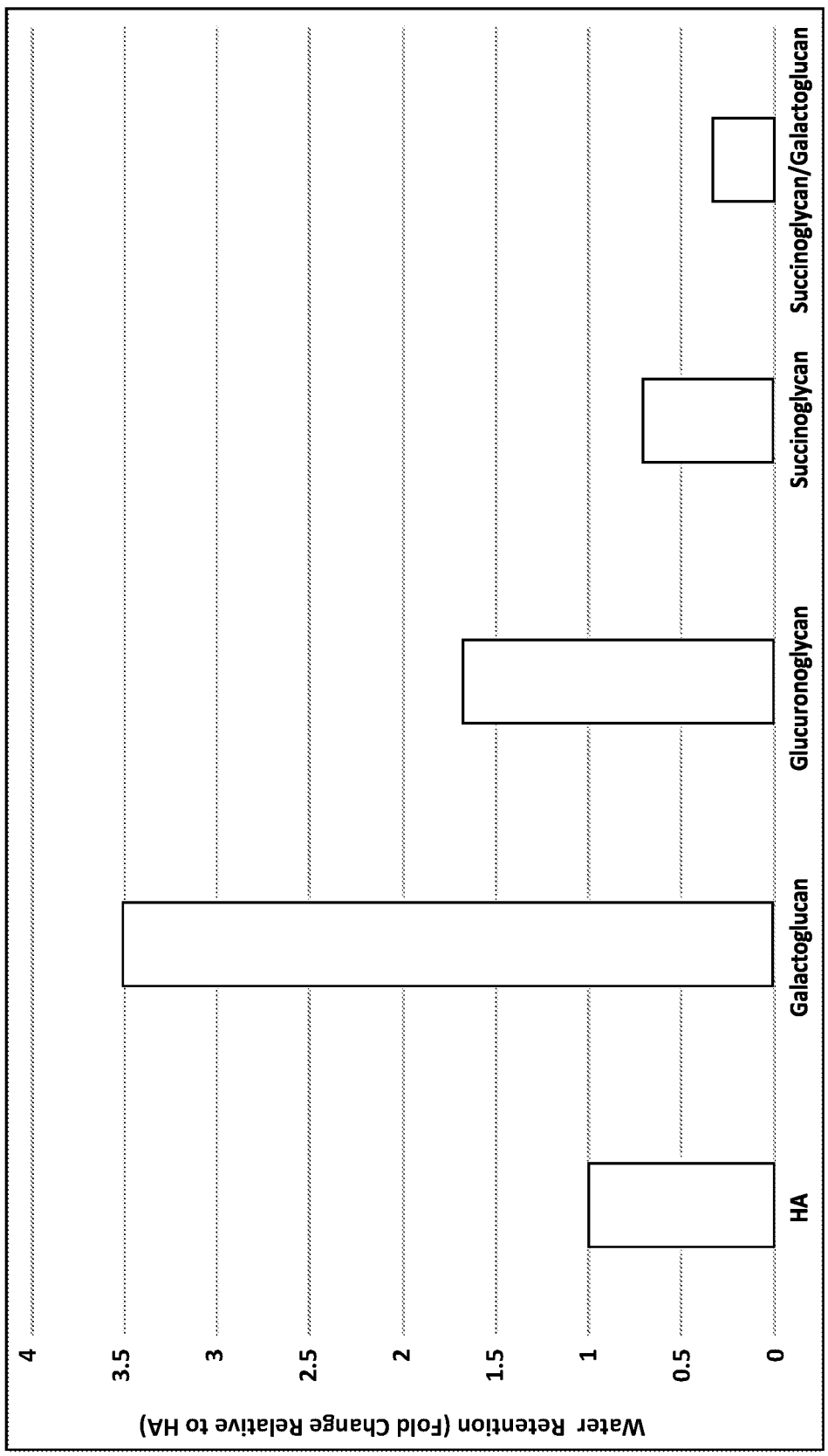
FIG. 3. Water absorption of isolated and mixed biopolymers compared to HA. The ability to bind water, as measured by mass increase, was determined for individual and mixed biopolymers. Mass increase for each biopolymer was divided by the mass increase of hyaluronic acid (HA) to derive relative fold change in water retention.

FIG. 3 shows that the WBC of isolated galactoglucan is increased by as much as 3.5-fold in comparison to HA. This WBC value was replicable across multiple experiments. The raw percent increase in mass was 650% for galactoglucan, which was substantially higher than the 185% increase measured for HA. After further incubation in the humidified chamber, the mass increase for galactoglucan reached as high as 720% of its initial mass. Results were similar when galactoglucan was derived from multiple carbon sources including glucose, sucrose, and corn syrup. Glucuronoglycan, isolated from *S. fredii*, showed a 1.7-fold increase in water binding relative to HA. The raw value for percent mass increase for glucuronoglycan was 311%. Isolated succinoglycan, in contrast to galactoglucan and glucuronoglycan, displayed decreased water binding in comparison to HA (0.7-fold decrease or 129% raw mass increase), and a mixture of succinoglycan and galactoglucan was reduced (0.3-fold decrease or 60% raw mass increase) even further. In the case of galactoglucan, the improved WBC was only observed when galactoglucan was purified independently, and not as the naturally occurring mixture of both galactoglucan and succinoglycan from *S. meliloti*.

Figure 4:
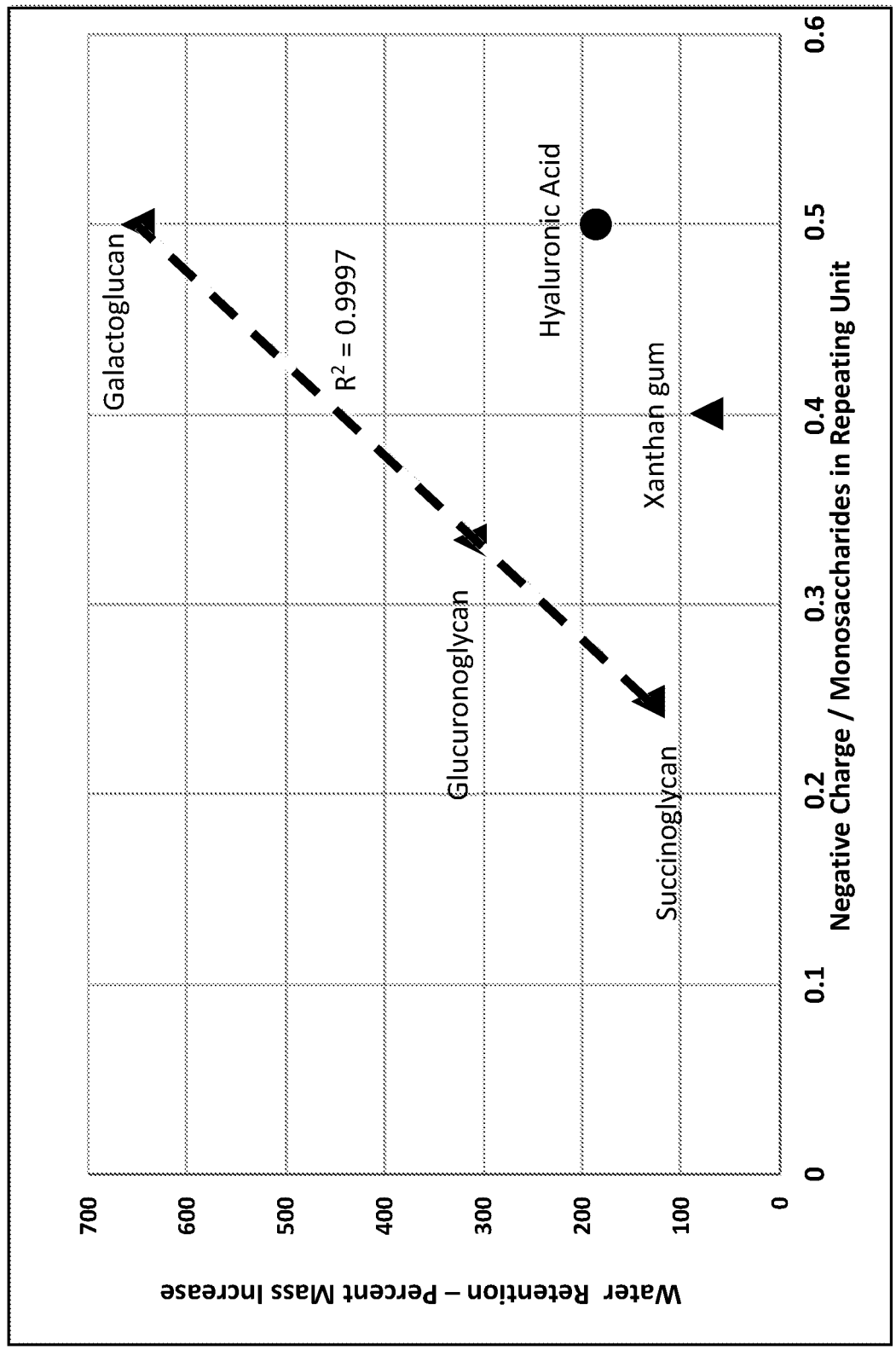
FIG. 4. Correlation between negative charge and water absorption. The charge of each biopolymer was calculated at physiological pH based on pKa of the acidic modifying group or sugar acid. This value was then divided by the number of sugar residues in a repeating unit to generate a ratio for each biopolymer. Charge density was plotted against the percent mass increase of each biopolymer.

Although monosaccharide type and content, chemical modifications, glycosidic linkages, and molecular weight may all affect the behavior of a biopolymer, for the biopolymers derived from these species of Rhizobiaceae, the degree of negative charge appears to be a predominant factor in WBC. FIG. 4 shows that for the *S. meliloti* and *S. fredii* biopolymers, there is a correlation between negative charge and water binding performance. For values on the x-axis, negative charge for each repeating unit was calculated based on the pKa of chemical groups or sugar acids at physiological pH. For example, the two glucuronic acids and the pyruvate modification of glucuronoglycan each contribute one negative charge at neutral pH, and therefore the ratio of negative charge to total sugars in the repeating unit is 1:3, or 0.33. For galactoglucan, this ratio is 1:2, and for succinoglycan this ratio is 1:4. These ratios were plotted against the values for percent mass increase of each biopolymer. As shown in FIG. 4, galactoglucan, the molecule with the highest ratio of negative charge to monosaccharides in the repeating unit had the highest capacity for water binding. Other rhizobial biopolymers fit precisely upon this trendline with a high $R^2$ value. Hyaluronic acid (gray circle), which also has a charge to monosaccharide ratio of 1:2, did not fit on the trendline, indicating that for this molecule, something other than or in addition to charge ratio affects water retention. Xanthan gum (Modernist Pantry) displayed poor water binding capacity in comparison to HA, and also did not fit on the trendline.

FIG. 5 shows the structure of a non-pyruvylated galactoglucan molecule (NP-galactoglucan), derived from an *S. meliloti* strain with the wgaE gene excised. The NP-galactoglucan molecule also retained more water than the HA control, although not to the extent of the fully pyruvylated galactoglucan. Compared to HA, the NP-galactoglucan molecule displayed a 1.7-fold increase in the ability to bind water.

Example 6. Cytotoxicity

To test for cytotoxicity, biopolymers were purified according to Example 3 and resuspended in a Ca-, Mg-free solution of PBS at a concentration of 1% (w/v). These solutions were then heat pasteurized for 30 minutes at 60° C. in a water bath. The cytotoxicity assay described below was carried out at Pacific Biolabs in Hercules, CA.

Test Procedure: A sterile filter paper with a flat surface measuring 1.0 cm2 total surface area was saturated with ~0.1 mL of the test solution and placed directly on the cell culture monolayer in the center of a 10 cm2 well. Triplicate preparations were prepared. Triplicate positive and negative controls were tested in the same manner as the test articles. All wells were incubated for not less than 24 hours at 37±1° C. in a humidified incubator with 5±1% CO2. After incubation, the test articles and controls were gently removed from the wells. The cell cultures were examined under an inverted microscope with 100× magnification for cytotoxic response. The response was graded on a scale of 0-4. The achievement of a numerical grade greater than 2 is considered a cytotoxic effect.

This study was conducted according to ISO 10993-5: 2009. A value of 0 is considered no reactivity, and a value of 1 is considered only slightly reactive. FIG. 6 shows that isolated succinoglycan, galactoglucan, glucuronoglycan, and a mixture of succinoglycan and galactoglucan are not cytotoxic according to this assay.

Example 7. Topical Formulations for Skin Care

Biopolymers and/or derivatives thereof are produced and purified according to Example 3. Purified biopolymers are added to the following commercially available lotion bases: Dermabase Cream™ (Paddock Laboratories), Crafter's Choice Basic Lotion Base (Crafter's Choice Brands LLC), and Stephenson Easy Lotion Base (Stephenson), or other similar base. These lotion bases represent a range of room temperature stable, oil-in-water emulsions for skin care. Biopolymers are either added directly to lotion bases or are resuspended in water or PBS (Ca-, Mg-free) prior to addition in order to achieve appropriate final concentrations. Typical formulations include biopolymers or derivatives at a final concentration between 0.1-2% (w/v).

Lotion Base Ingredients:

Dermabase Cream™—Purified water, mineral oil, petrolatum, cetostearyl alcohol, propylene glycol, sodium lauryl sulfate, isopropyl palmitate, imidazolidinyl urea, methylparaben and propylparaben.

Crafter's Choice™ Basic Lotion Base—Water, Cetearyl Alcohol, Glyceryl Stearate, Polysorbate-60, Stearyl Alcohol, Sunflower Oil, Allantoin, Propylene Glycol, Isopropyl Palmitate, Petrolatum, Diazolidinyl Urea, Methylparaben, Propylparaben, BHT, Carbomer, Benzophenone-4, Stearic Acid.

Stephenson Easy Lotion Base—Water, Sunflower Seed Oil, Polysorbate 20, Cetearyl Alcohol, Glyceryl Stearate, Phenoxyethanol, Carbomer, Potassium Sorbate, Sodium Hydroxide.

For skin hydration testing of biopolymers, the following oil-in-water base lotion was used: Distilled water, *Papaver Somniferum* (Poppy seed) Seed Oil, Glycerin, Pentylene Glycol (Plant based), Olive Squalane, Polyglyceryl-2 Stearate, Glyceryl Stearate, Stearyl Alcohol, Tocopherol, *Lonicera Japonica* (Honeysuckle) flower extract, *Lonicera caprifolium* (Honeysuckle) Flower Extract, galactoglucan 0.2% (w/v), Acacia Senegal Gum, Xanthan Gum, Sodium Phytate, Alcohol, and Lactic Acid.

Example 8. In Vivo Skin Hydration Studies

The biopolymer-containing lotion base formulations described in Example 7, as well as placebo compositions, are used for comparative in vivo testing of moisture content in skin. Placebo compositions for each lotion base containing biopolymer are generated by adding an equivalent volume of PBS or sterile water.

For skin hydration studies, subjects are instructed to apply a standard amount of lotion base containing biopolymer to the right side of their face, and the placebo composition to the left side of their face. Subjects are instructed to always apply the same composition to the same side of their face. Subjects apply these compositions twice per day for a defined duration of time and are instructed to refrain from using any other topical composition unrelated to the study compositions. Measurements of skin hydration are carried out using a Corneometer 825 (Courage and Khazaka).

Figure 7:
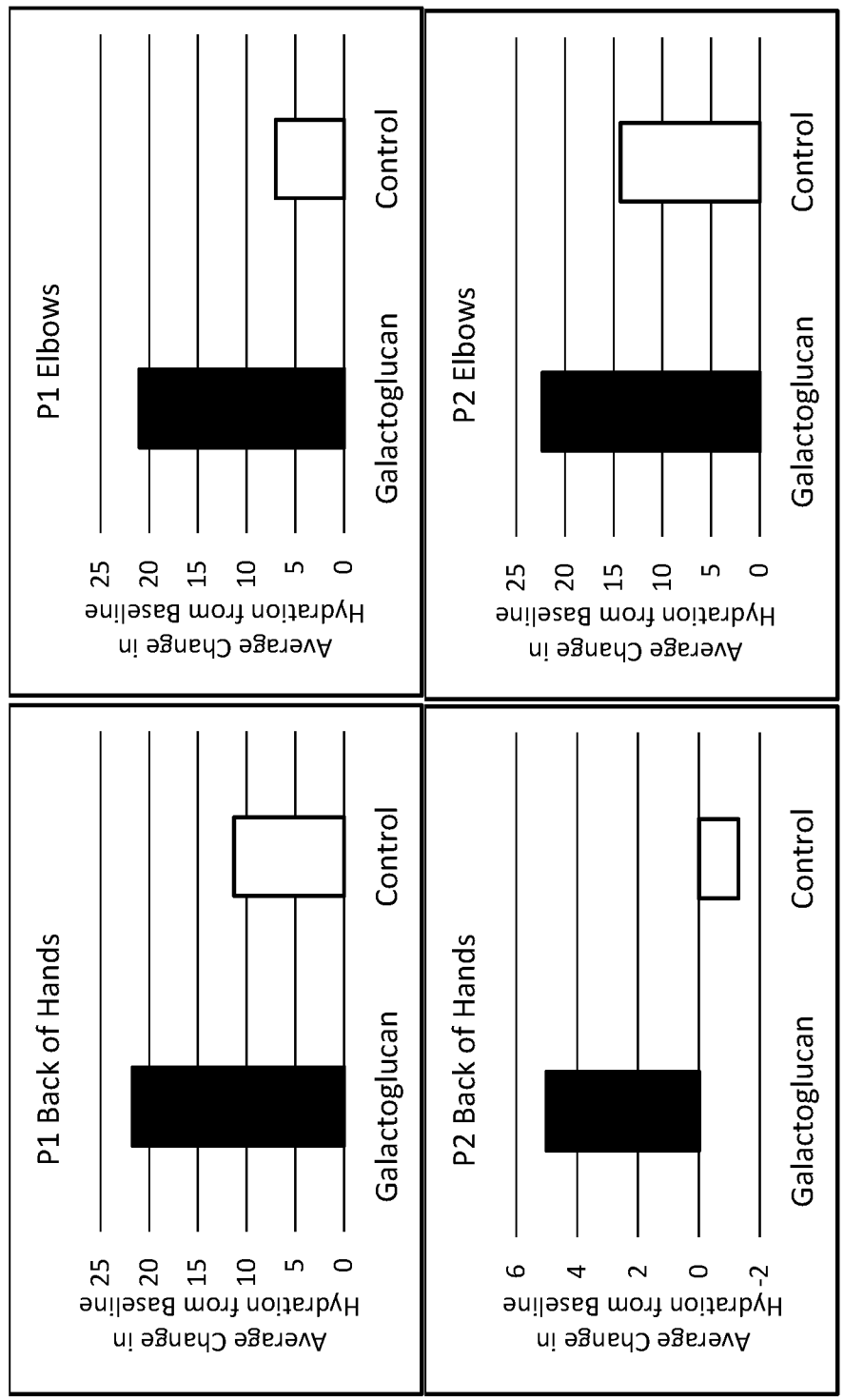
FIG. 7. Skin Hydration Measurements. Measurements were performed using a Corneometer 825 (Courage+ Khazaka). Two healthy volunteers applied lotion base containing either galactoglucan at 0.2% (w/v) or a control base (containing an equivalent amount of water) to two different areas of the body, hands and elbows, for a 48-hour period. Shown are the average values for changes in hydration (in a.u. as measured by the Corneometer) from the baseline measurements of each location on the body for each participant FIG. 8. Reduction in Appearance of Wrinkles with Galactoglucan Treatment. An image of the backs of the hand of participant P1 from Example 8. The circles highlight areas where reduction in the appearance of wrinkles can be observed.
Figure 8:
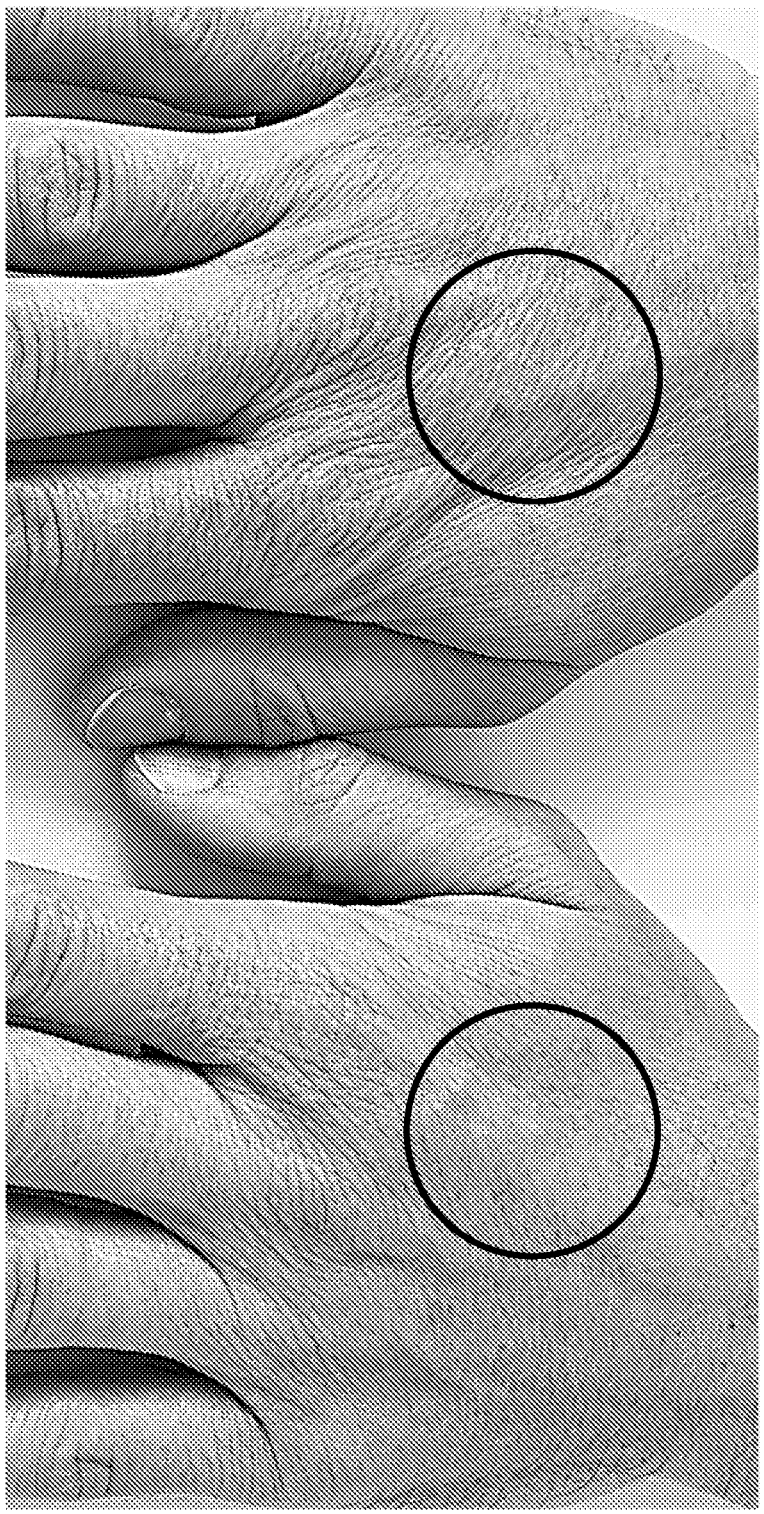

Galactoglucan was purified according to the procedures described above and used for skin hydration studies. Skin hydration was measured over a 48 hour period using the poppy seed oil formulation described in Example 7 containing either 0.2% (w/v) galactoglucan, or an equivalent amount of water as a control. Baseline skin hydration measurements (in a.u. from Corneometer 825) for two healthy volunteers, male age 47 (P1) and female age 49 (P2), were taken prior to commencement of the study. For this study, Corneometer measurements in a.u. typically ranged between 20 and 50, with a maximum value of 120 for the instrument. Participants were instructed to apply approximately 0.3 ml to two different locations on the body—back of hands and elbows. Test and control samples were applied 4 times per day, and the change in skin hydration was monitored prior to each application. FIG. 7 shows the average values for the change in hydration from the baseline for each location on the body for measurements taken after 24 hours of treatment. Treatment with the lotion base containing galactoglucan resulted in a consistent increase in hydration value for both locations on the body for both P1 and P2 in comparison to the lotion base control. It is worth noting that after 24 hours of treatment, trends in hydration became well established, suggesting that the hydration effect is cumulative and that longer periods of treatment would result in even greater hydration differences between lotion containing galactoglucan and the control. FIG. 8 shows an image of the backs of the hands of participant P1 after 36 hours of treatment, where a clear reduction in the appearance of wrinkles can be observed on the galactoglucan-treated hand in comparison to the hand treated with the control lotion base. The circles highlight areas where reduction in the appearance of wrinkles is particularly evident. Participants reported no redness, irritation, swelling, sensitivity, or discomfort with either experimental or control treatment.

Example 9. In Vitro Percutaneous Absorption of Biopolymers

Ex vivo dermal studies are used to assess skin penetration and to rank biopolymers in terms of permeability or accumulation, and to optimize formulations for efficacy. Studies are performed with human or porcine skin in Franz diffusion cells (Franz 1975) to assess percutaneous absorption. Biopolymer formulations are applied to the upper (external) surface with the Franz cell, and samples are removed at pre-determined time points from the reservoir containing buffer that is in contact with the lower (serosal) surface, and measured. Control polymers or other compounds are either co-dosed (if the test biopolymer is in solution) or run in parallel (if the test biopolymer is in some other type of formulation) for quality control. The skin may be extracted at the end of the study to quantify accumulation of the test compound.

Franz Cell assays were conducted using non-pyruvylated galactoglucan samples. Specifically, excised human cadaver skin from a single donor was measured for thickness and then mounted in Franz vertical diffusion cells that were thermostatically controlled at 37° C. (FDC-6, Logan instruments, Somerset, NJ). Receptor solution (PBS, pH 7.4) was added, and allowed to equilibrate for 30 minutes at 37° C. (to reach skin surface temperature of 32° C.). After the equilibration period, the entire receptor solution volume (approximately 11 ml) was removed, discarded, and replaced with fresh, pre-warmed receptor solution to remove endogenous background released into the buffer prior to initiation of the experiment.

Dosing solution was prepared by adding 5% (w/v) biopolymer to PBS, pH 7.4 and incubating at 50° C. for 30 minutes. 1 ml of dosing solution was added to each donor chamber. The total amount of biopolymer for each chamber was thus 50 mg. Donor solution was sampled at 0, 8, and 24 hours. Receptor solution was sampled at 0.5, 1, 2, 4, 8, and 24 hrs. After 24 hours, tissue was de-mounted and rinsed briefly in blank PBS after the permeation duration, weighed, and stored individually at −20° C. For quantitation of biopolymer, the anthrone method (Morris 1948) was used in conjunction with the Carrez reagent (EMD Millipore) to reduce protein background in receptor samples. The anthrone method is commonly used to detect the presence of carbohydrate in solution. For receptor samples, 4 μL of Carrez reagent I was added to 4004 of sample in a 1.5 mL tube and the tube was mixed by vortexing. Another 4 μL of Carrez reagent II was then added and the tube mixed again. The reagent was neutralized with 2.5 μL of 1 N NaOH and tubes were centrifuged 5 minutes at 16,000×g. 625 μL of 0.2% anthrone in concentrated sulfuric acid was mixed with 325 μL of supernatant on ice. Samples were heated 15 minutes at 99° C. then cooled on ice.

To detect biopolymer that was retained in the skin, de-mounted samples were soaked in 1 mL PBS in a 2 mL tube at 37° C. for 4 hours then 4° C. for 3 days. The PBS was collected and centrifuged twice at 16,000×g for 5 min to remove debris. The samples were clarified using the Carrez reagent as above then diluted 10-fold in PBS.

Figure 9:
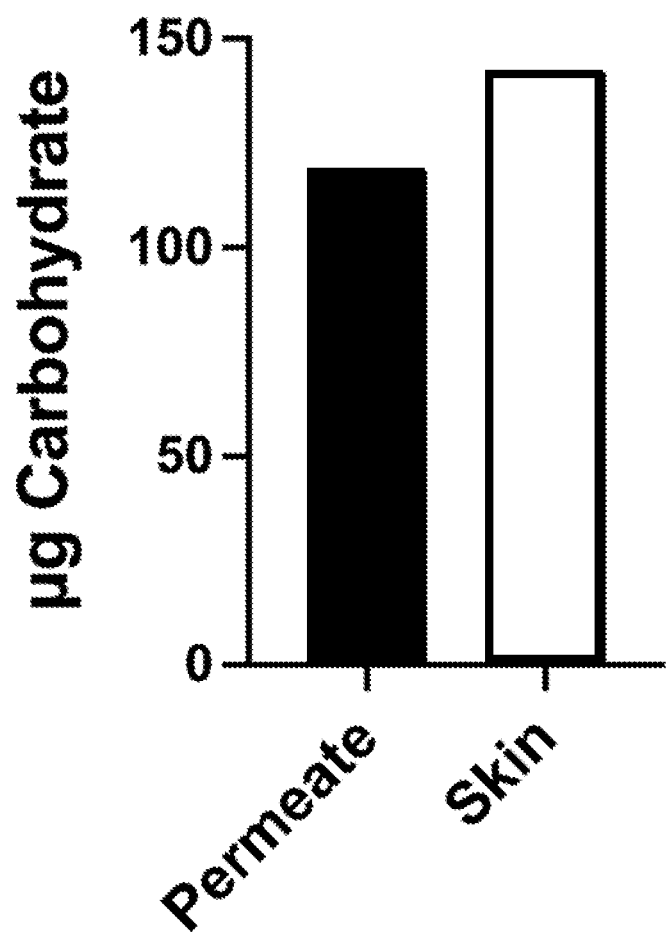
FIG. 9. Transdermal Penetration and Skin Retention Assay Results. Unidirectional permeability across ex-vivo human skin tissue was determined using Franz Cells. Results are shown for the amount of carbohydrate in a representative receptor chamber (permeate) after 4 hours of treatment with a donor solution of 5% (w/v) of non-pyruvylated galactoglucan. After completion of the Franz Cell Assay, the skin sample was rinsed and then soaked in PBS to elute carbohydrate that was absorbed or associated with the skin surface. Total carbohydrate in receptor solution or in eluted skin sample was determined using the anthrone assay. Background levels from control receptor chambers and skin samples were subtracted to derive the reported values.

For all samples, absorbance was measured at 620 nm and carbohydrate concentration was determined by comparison to a standard curve that had been clarified using the Carrez reagent. Background absorbance for control Franz Cells (with no biopolymer) was calculated and subtracted from values to derive carbohydrate concentration. FIG. 9 shows representative results from a receptor chamber after four hours of incubation (permeate). Carbohydrate detected in this sample indicates that biopolymer had penetrated the epidermal layer. The highest concentration of biopolymer in the receptor chamber was typically observed at these time points. FIG. 9 also shows that a certain amount of biopolymer was either in or associated with the skin itself (skin) after the de-mounted sample was soaked in PBS as described above. These findings show that a fraction of the material in the donor chamber of the Franz Cell fully permeated the skin samples, and another fraction was retained in or associated with the skin sample. Without intending to be bound by any particular theory, the skin-penetrating fraction of non-pyruvylated galactoglucan may be the lowest molecular weight in the sample, and higher molecular weight fractions may be absorbed by and/or retained upon the surface of the epidermis.

I claim:

1. A method of treating a skin condition in a subject, comprising applying a topical composition to the skin of the subject, wherein the topical composition comprises a biopolymer preparation comprising a biopolymer that is composed of repeating disaccharide units comprising glucose and galactose, wherein at least 60% of the glucose is acetylated and at least 40% of the galactose is pyruvylated, wherein the glucose and galactose are linked by β-1,3 glycosidic bonds and α-1,3 glycosidic bonds, and wherein the biopolymer preparation is less than 25% succinoglycan.

2. The method of claim 1, wherein the biopolymer preparation comprises a biopolymer that is composed of repeating disaccharide units of the structure:

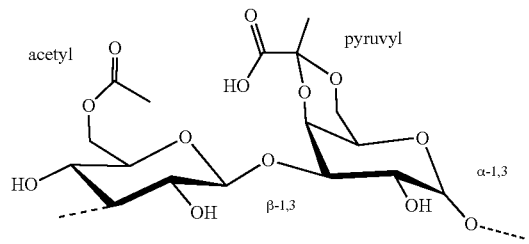

wherein the dotted lines represent the bonds between disaccharide units; wherein no more than 40% of the disaccharide units lack the acetyl moiety; and where in no more than 60% of the disaccharide units lack the pyruvyl moiety.

3. The method of claim 1, wherein the biopolymer preparation is less than 5% succinoglycan.

4. The method of claim 1, wherein the topical composition comprises one or more viscosifiers, stabilizers, emulsifiers, emollients, humectants, rheology modifiers, film formers, antioxidants, additives, actives, butters, essential oils, infused oils, clays, muds, extracts, hydrosol waters, exfoliants, supplements, waxes, thickeners, salts, minerals, acids, bases, carrier and fixed oils, surfactants, preservatives, pearlizers, conditioning agents, structuring agents, whitening agents, moisturizers, osmolytes, occlusives, cleansers, colorants, pigments, fragrances, UV-A and UV-B screens, and/or nourishing agents.

5. The method of claim 1, wherein the topical composition is a cream, lotion, serum, ointment, balm, tincture, liniment, shampoo, soap, conditioner, sunscreen, rinse, deodorant, or cosmetic.

6. The method of claim 1, wherein the skin condition is one or more of dry skin, wrinkled skin, sagging skin, aged skin, scarred skin, injured skin, blemished skin, acne, and/or sunburned skin.

7. The method of claim 1, wherein the skin condition is an inflammatory skin condition.

8. The method of claim 7, wherein the inflammatory skin condition is psoriasis, eczema, or atopic dermatitis.

9. The method of claim 1, wherein the topical composition is applied to the face, ears, forehead, neck, arms, upper chest, legs, feet, and/or hands of the subject.

10. The method of claim 1, wherein the topical composition reduces transepidermal water loss, reverses transepidermal water loss, improves epidermal water retention, reduces appearance of wrinkles, reduces skin sagging, increases skin smoothness, increases swelling of the skin, improves skin suppleness, improves skin texture, reduces skin blemishes, and/or reduces skin dryness.

11. The method of claim 3, wherein the topical composition comprises 0.01%-10% 0.05% 5% w/w of the biopolymer.

12. The method of claim 3, wherein the topical composition comprises one or more viscosifiers, stabilizers, emulsifiers, emollients, humectants, rheology modifiers, film formers, antioxidants, additives, actives, butters, essential oils, infused oils, clays, muds, extracts, hydrosol waters, exfoliants, supplements, waxes, thickeners, salts, minerals, acids, bases, carrier and fixed oils, surfactants, preservatives, pearlizers, conditioning agents, structuring agents, whitening agents, moisturizers, osmolytes, occlusives, cleansers, colorants, pigments, fragrances, UV-A and UV-B screens, and/or nourishing agents.

13. The method of claim 3, wherein the topical composition is a cream, lotion, serum, ointment, balm, tincture, liniment, shampoo, soap, conditioner, sunscreen, rinse, deodorant, or cosmetic.

14. A method of preventing dry skin and/or transepidermal water loss in a subject, comprising applying a topical composition to the skin of the subject, wherein the topical composition comprises a biopolymer preparation comprising a biopolymer that is composed of repeating disaccharide units comprising glucose and galactose, wherein at least 60% of the glucose is acetylated and at least 40% of the galactose is pyruvylated, wherein the glucose and galactose are linked by β-1,3 glycosidic bonds and α-1,3 glycosidic bonds, and wherein the biopolymer preparation is less than 25% succinoglycan of claim 11.

15. The method of claim 14, wherein the topical composition is applied to the face, ears, forehead, neck, arms, upper chest, legs, feet, and/or hands of the subject.

16. The method of claim 1, wherein the biopolymer preparation is substantially free of succinoglycan.

17. The method of claim 1, wherein at least 65% of the glucose is acetylated.

18. The method of claim 1, wherein at least at least 90% of the galactose is pyruvylated.

19. The method of claim 2, wherein the biopolymer preparation is less than 5% succinoglycan.

20. The method of claim 1, wherein the biopolymer preparation is less than 3% succinoglycan.

21. The method of claim 2, wherein the biopolymer preparation is less than 3% succinoglycan.

22. The method of claim 1, wherein the topical composition comprises 0.05%-5% w/w of the biopolymer.

23. The method of claim 2 wherein the topical composition comprises 0.05%-5% w/w of the biopolymer.

24. The method of claim 3, wherein the topical composition reduces appearance of wrinkles, increases skin smoothness, improves skin texture, reduces skin blemishes, and/or reduces skin dryness.

25. The method of claim 3, wherein the skin condition is dry skin and the topical composition reduces skin dryness.

26. The method of claim 3, wherein the skin condition is wrinkled skin, and the topical composition reduces appearance of wrinkles.

27. The method of claim 6, wherein the skin condition is aged skin, and the topical composition is anti-aging.

28. The method of claim 11, wherein the topical composition comprises one or more viscosifiers, stabilizers, emulsifiers, emollients, humectants, rheology modifiers, film formers, antioxidants, additives, actives, butters, essential oils, infused oils, clays, muds, extracts, hydrosol waters, exfoliants, supplements, waxes, thickeners, salts, minerals, acids, bases, carrier and fixed oils, surfactants, preservatives, pearlizers, conditioning agents, structuring agents, whitening agents, moisturizers, osmolytes, occlusives, cleansers, colorants, pigments, fragrances, UV-A and UV-B screens, and/or nourishing agents.

29. The method of claim 11, wherein the skin condition is one or more of dry skin, wrinkled skin, sagging skin, aged skin, scarred skin, injured skin, blemished skin, acne, and/or sunburned skin.

30. The method of claim 11, wherein the skin condition is an inflammatory skin condition.

31. The method of claim 30, wherein the inflammatory skin condition is psoriasis, eczema, or atopic dermatitis.

32. The method of claim 11, wherein the topical composition is applied to the face, ears, forehead, neck, arms, upper chest, legs, feet, and/or hands of the subject.

33. The method of claim 11, wherein the topical composition reduces transepidermal water loss, reverses transepidermal water loss, improves epidermal water retention, reduces appearance of wrinkles, reduces skin sagging, increases skin smoothness, increases swelling of the skin, improves skin suppleness, improves skin texture, reduces skin blemishes, and/or reduces skin dryness.

34. The method of claim 11, wherein the topical composition reduces appearance of wrinkles, increases skin smoothness, improves skin texture, reduces skin blemishes, and/or reduces skin dryness.

35. The method of claim 11, wherein the skin condition is dry skin and the topical composition reduces skin dryness.

36. The method of claim 11, wherein the skin condition is wrinkled skin, and the topical composition reduces appearance of wrinkles.

37. The method of claim 11, wherein the skin condition is aged skin, and the topical composition is anti-aging.

38. The method of claim 14, wherein the biopolymer preparation comprises a biopolymer that is composed of repeating disaccharide units of the structure:

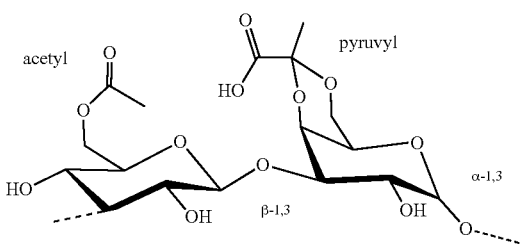

wherein the dotted lines represent the bonds between disaccharide units; wherein no more than 40% of the disaccharide units lack the acetyl moiety; and wherein no more than 60% of the disaccharide units lack the pyruvyl moiety.

39. The method of claim 14, wherein the biopolymer preparation is less than 5% succinoglycan.

40. The method of claim 14, wherein the topical composition comprises one or more viscosifiers, stabilizers, emulsifiers, emollients, humectants, rheology modifiers, film formers, antioxidants, additives, actives, butters, essential oils, infused oils, clays, muds, extracts, hydrosol waters, exfoliants, supplements, waxes, thickeners, salts, minerals, acids, bases, carrier and fixed oils, surfactants, preservatives, pearlizers, conditioning agents, structuring agents, whitening agents, moisturizers, osmolytes, occlusives, cleansers, colorants, pigments, fragrances, UV-A and UV-B screens, and/or nourishing agents.

41. The method of claim 14, wherein the topical composition is a cream, lotion, serum, ointment, balm, tincture, liniment, shampoo, soap, conditioner, sunscreen, rinse, deodorant, or cosmetic.

42. The method of claim 14, wherein the topical composition comprises 0.05%-5% w/w of the biopolymer.

43. The method of claim 1, wherein the topical composition comprises 0.05%-5% w/w of the biopolymer.

44. The method of claim 2, wherein the topical composition comprises 0.01%-10% w/w of the biopolymer.

45. The method of claim 3, wherein the topical composition comprises 0.01%-10% w/w of the biopolymer.

46. The method of claim 14, wherein the topical composition comprises 0.01%-10% w/w of the biopolymer.

47. The method of claim 2, wherein the biopolymer preparation is substantially free of succinoglycan.

* * * * *

UNITED STATES PATENT AND TRADEMARK OFFICE
CERTIFICATE OF CORRECTION

PATENT NO. : 12,202,912 B2
APPLICATION NO. : 18/183517
DATED : January 21, 2025
INVENTOR(S) : Derek H. Wells Page 1 of 1

It is certified that error appears in the above-identified patent and that said Letters Patent is hereby corrected as shown below:

In the Claims

In Claim 11, Column 29, Lines 24-26 should read:
--The method of claim 3, wherein the topical composition comprises 0.01%-10% w/w of the biopolymer.--

Signed and Sealed this
Eleventh Day of March, 2025

Coke Morgan Stewart
*Acting Director of the United States Patent and Trademark Office*